United States Patent
Bergnes et al.

(10) Patent No.: US 7,208,487 B2
(45) Date of Patent: Apr. 24, 2007

(54) COMPOUNDS, COMPOSITIONS AND METHODS

(75) Inventors: Gustave Bergnes, Pacifica, CA (US); Dashyant Dhanak, Collegeville, PA (US); Steven David Knight, Collegeville, PA (US); Pu Ping Lu, Foster City, CA (US); David J. Morgans, Jr., Los Altos, CA (US); Kenneth Allen Newlander, Collegeville, PA (US)

(73) Assignee: Cytokinetics, Incorporated, South San Francisco, CA (US)

( * ) Notice: Subject to any disclaimer, the term of this patent is extended or adjusted under 35 U.S.C. 154(b) by 0 days.

(21) Appl. No.: 10/538,228

(22) PCT Filed: Dec. 12, 2003

(86) PCT No.: PCT/US03/39708

§ 371 (c)(1),
(2), (4) Date: Jun. 8, 2005

(87) PCT Pub. No.: WO2004/055008

PCT Pub. Date: Jul. 1, 2004

(65) Prior Publication Data

US 2006/0052360 A1    Mar. 9, 2006

Related U.S. Application Data

(60) Provisional application No. 60/435,001, filed on Dec. 19, 2002, provisional application No. 60/433,494, filed on Dec. 13, 2002.

(51) Int. Cl.
*C07D 403/06* (2006.01)
*A61K 31/57* (2006.01)

(52) U.S. Cl. ............................ 514/211.03; 514/211.08; 514/211.15; 514/212.08; 540/488; 540/492; 540/524

(58) Field of Classification Search ................ 540/488, 540/492, 524; 514/211.03, 211.08, 211.15, 514/212.08
See application file for complete search history.

(56) References Cited

FOREIGN PATENT DOCUMENTS

WO   WO 03/099211 A2   12/2003

*Primary Examiner*—Bruck Kifle
(74) *Attorney, Agent, or Firm*—Finnegan, Henderson, Farabow, Garrett & Dunner, LLP

(57) ABSTRACT

Compounds useful for treating cellular proliferative diseases and disorders by modulating the activity of KSP are disclosed.

13 Claims, No Drawings

COMPOUNDS, COMPOSITIONS AND METHODS

CROSS-REFERENCE TO RELATED APPLICATIONS

This application claims the benefit of co-pending provisional U.S. Application Ser. No. 60/433,494, filed Dec. 13, 2002, and 60/435,001, filed Dec. 19, 2002, each incorporated herein by reference.

FIELD OF THE INVENTION

This invention relates to compounds that are inhibitors of the mitotic kinesin KSP and are useful in the treatment of cellular proliferative diseases, for example cancer, hyperplasias, restenosis, cardiac hypertrophy, immune disorders, fungal disorders, and inflammation.

BACKGROUND OF THE INVENTION

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase 1 inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described (Blangy, et al., Cell, 83:1159–69 (1995); Whitehead, et al., Arthritis Rheum., 39:1635–42 (1996); Galgio et al., J. Cell Biol., 135:339–414 (1996); Blangy, et al., J Biol. Chem., 272:19418–24 (1997); Blangy, et al., Cell Motil Cytoskeleton, 40:174–82 (1998); Whitehead and Rattner, J. Cell Sci., 111:2551–61 (1998); Kaiser, et al., JBC 274:18925–31 (1999); GenBank accession numbers: X85137, NM004523 and U37426), and a fragment of the KSP gene (TRIP5) has been described (Lee, et al., Mol Endocrinol., 9:243–54 (1995); GenBank accession number L40372). Xenopus KSP homologs (Eg5), as well as Drosophila KLP61 F/KRP1 30 have been reported.

Mitotic kinesins are attractive targets for the discovery and development of novel antimitotic chemotherapeutics. Accordingly, it is an object of the present invention to provide compounds, compositions and methods useful in the inhibition of KSP, a mitotic kinesin.

SUMMARY OF THE INVENTION

In accordance with the objects outlined above, the present invention provides compounds, compositions and methods that can be used to treat diseases of proliferating cells. The compounds are KSP inhibitors, particularly human KSP inhibitors.

In one aspect, the invention relates to methods for treating cellular proliferative diseases, for treating disorders by modulating the activity of KSP, and for inhibiting KSP kinesin. In one aspect, the methods employ compounds represented by Formula I, or a pharmaceutically acceptable derivative (including pharmaceutically acceptable salts) or a solvate thereof:

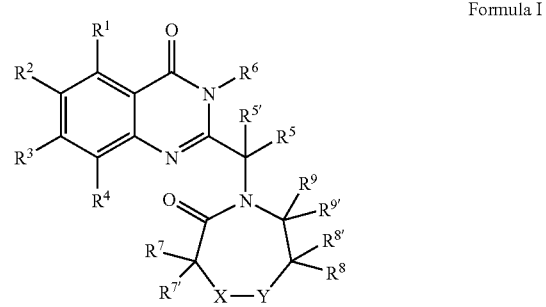

Formula I wherein:

$R^1$, $R^2$, $R^3$ and $R^4$ are each independently chosen from hydrogen, optionally substituted alkyl, optionally substituted alkoxy, halogen, hydroxyl, nitro, cyano, dialkylamino, alkylsulfonyl, alkylsulfonamido, alkylthio, carboxyalkyl, carboxamido, aminocarbonyl, optionally substituted aryl and optionally substituted heteroaryl;

$R^5$ and $R^{5'}$ are each independently chosen from hydrogen, optionally substituted alkyl, optionally substituted aryl, optionally substituted aralkyl, optionally substituted heteroaryl, and optionally substituted heteroaralkyl; or $R^5$ and $R^{5'}$ taken together form an optionally substituted 3- to 7-membered carbocyclic ring;

$R^6$ is hydrogen, optionally substituted alkyl, optionally substituted aryl, optionally substituted aralkyl, optionally substituted heteroaryl, or optionally substituted heteroaralkyl;

$R^7$, $R^{7'}$, $R^8$, $R^{8'}$, $R^9$ and $R^{9'}$ are each independently chosen from hydrogen, optionally substituted alkyl, optionally substituted aryl, optionally substituted aralkyl, optionally substituted heteroaryl, and optionally substituted heteroaralkyl;

X and Y are each independently chosen from $C(R^{10})(R^{11})$, $N(R^{12})$, O and S, wherein $R^{10}$ and $R^{11}$ are each independently selected from H, optionally substituted alkyl, optionally substituted aryl and optionally substituted heteroaryl; and $R^{12}$ is H, optionally substituted alkyl optionally substituted aralkyl, optionally substituted heteroaralkyl optionally substituted alkylcarbonyl, optionally substituted arylcarbonyl, optionally substituted heteroarylcarbonyl, optionally substituted aralkylcarbonyl, optionally substituted heteroaralkylcarbonyl, optionally substituted alkoxycarbonyl, optionally substituted aryloxycarbonyl, optionally substituted heteroaryloxycarbonyl, optionally substituted aralkyloxycarbonyl, or optionally substituted heteroaralkyloxycarbonyl.

In another aspect, the methods employ compounds represented by Formula II, or a pharmaceutically acceptable derivative (including pharmaceutically acceptable salts) or a solvate thereof:

Formula II

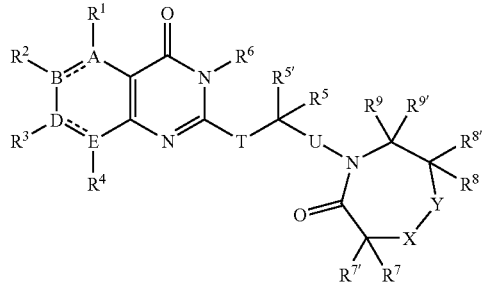

wherein:

T and U are independently a covalent bond, —C(O)—, or optionally substituted alkylene;

A, B, D and E are independently N, C, CH, O, S or absent, provided that:

no more than one of A, B, D or E is absent;

no more than two of A, B, D or E are —N═, and

A, B, D or E can be O or S only when one of A, B, D or E is absent; and

X, Y, $R^1$ to $R^9$ and $R^{5'}$, $R^{7'}$, $R^{8'}$ and $R^{9'}$ are as defined with regard to Formula I, provided that $R^1$, $R^2$, $R^3$ or $R^4$ is absent where A, B, D or E, respectively, is —N═, O, S or absent.

Compounds of Formula I and II include single stereoisomers and mixtures of stereoisomers thereof.

In one aspect, the invention relates to methods for treating cellular proliferative diseases, for treating disorders that can be treated by modulating KSP kinesin activity, and for inhibiting KSP by the administration of a therapeutically effective amount of a compound of Formula I or II or a pharmaceutically acceptable derivative (including pharmaceutically acceptable salts) or a solvate thereof. Such diseases and disorders include cancer, hyperplasia, restenosis, cardiac hypertrophy, immune disorders, fungal disorders and inflammation.

In another aspect, the invention relates to compounds useful in inhibiting KSP kinesin. The compounds have the structures shown above in Formula I or II, or a pharmaceutically acceptable derivative or solvate thereof.

The invention also relates to a pharmaceutical composition containing a therapeutically effective amount of a compound of Formula I or II or a pharmaceutically acceptable derivative (e.g., salt) or solvate thereof, admixed with at least one pharmaceutically acceptable excipient.

Yet another aspect of the invention relates to a kit comprising a compound of Formula I or II, or a pharmaceutically acceptable derivative (e.g., salt) or solvate thereof, and package insert or other labeling including directions for treating a cellular proliferative disease by administering an effective (particularly a therapeutically effective) amount of the compound, derivative or solvate. In one particular such aspect, the compound, derivative or solvate is provided as a pharmaceutical composition.

In an additional aspect, the present invention provides methods of screening for compounds that will bind to a KSP kinesin, for example compounds that will displace or compete with the binding of the compounds of the invention. The methods comprise combining a labeled compound of the invention, a KSP kinesin, and at least one candidate agent and determining the binding of the candidate bioactive agent to the KSP kinesin.

In a further aspect, the invention provides methods of screening for modulators of KSP kinesin activity. The methods comprise combining a compound of the invention, a KSP kinesin, and at least one candidate agent and determining the effect of the candidate bioactive agent on the KSP kinesin activity.

DETAILED DESCRIPTION OF THE INVENTION

Compounds of the Present Invention

The present invention is directed to a class of novel compounds that are inhibitors of one or more mitotic kinesins. By inhibiting one or more mitotic kinesins, but not other kinesins (e.g., transport kinesins), specific inhibition of cellular proliferation is accomplished. While not intending to be bound by any theory, the present invention capitalizes on the finding that perturbation of mitotic kinesin function causes malformation or dysfunction of mitotic spindles, frequently resulting in cell cycle arrest and cell death. According to one embodiment of the invention, the compounds described herein inhibit the mitotic kinesin, KSP. In another embodiment, the compounds inhibit the mitotic kinesin, KSP, as well as modulating one or more of the human mitotic kinesins selected from the group consisting of HSET (see, U.S. Pat. No. 6,361,993, which is incorporated herein by reference); MCAK (see U.S. Pat. No. 6,331,424, which is incorporated herein by reference); CENP-E (see, PCT Publication No. WO 99/13061, which is incorporated herein by reference); Kif4 (see, U.S. Pat. No. 6,440,684, which is incorporated herein by reference); MKLP1 (see, U.S. Pat. No. 6,448,025, which is incorporated herein by reference); Kif15 (see, U.S. Pat. No. 6,355,466, which is incorporated herein by reference); Kid (see, U.S. Pat. No. 6,387,644, which is incorporated herein by reference); Mpp1, CMKrp, KinI-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and RabK6.

The methods of inhibiting a human KSP kinesin comprise contacting an inhibitor of the invention with a kinesin, particularly a human kinesin, preferably human KSP or fragments and variants thereof. The inhibition can be of the ATP hydrolysis activity of the KSP kinesin and/or the mitotic spindle formation activity, such that the mitotic spindles are disrupted. Meiotic spindles may also be disrupted.

An object of the present invention is to develop inhibitors of mitotic kinesins, in particular KSP and especially human KSP, for the treatment of disorders associated with cell proliferation. Traditionally, dramatic improvements in the treatment of cancer, one type of cellular proliferative disorder, have been associated with identification of therapeutic agents acting through novel mechanisms. Examples of this include not only the taxane class of agents that appear to act on microtubule formation, but also the camptothecin class of topoisomerase I inhibitors. The compounds, compositions and methods described herein can differ in their selectivity and are preferably used to treat diseases of cellular proliferation, including, but not limited to cancer, hyperplasias, restenosis, cardiac hypertrophy, immune disorders, fungal disorders and inflammation.

Accordingly, the present invention relates to methods employing compounds represented by Formula I, or a pharmaceutically acceptable derivative or solvate thereof:

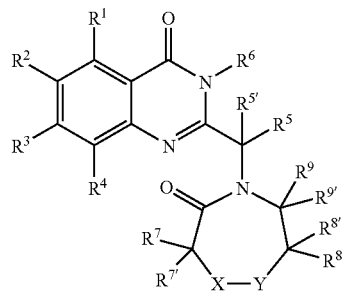

Formula I wherein:

$R^1$, $R^2$, $R^3$ and $R^4$ are each independently chosen from hydrogen, optionally substituted alkyl, optionally substituted alkoxy, halogen, hydroxyl, nitro, cyano, dialkylamino, alkylsulfonyl, alkylsulfonamido, alkylthio, carboxyalkyl, carboxamido, aminocarbonyl, optionally substituted aryl and optionally substituted heteroaryl;

$R^5$ and $R^{5'}$ are each independently chosen from hydrogen, optionally substituted alkyl, optionally substituted aryl, optionally substituted aralkyl, optionally substituted heteroaryl, and optionally substituted heteroaralkyl; or $R^5$ and $R^{5'}$ taken together form an optionally substituted 3- to 7-membered carbocyclic ring;

$R^6$ is hydrogen, optionally substituted alkyl, optionally substituted aryl, optionally substituted aralkyl, optionally substituted heteroaryl, or optionally substituted heteroaralkyl;

$R^7$, $R^{7'}$, $R^8$, $R^{8'}$, $R^9$ and $R^{9'}$ are each independently chosen from hydrogen, optionally substituted alkyl, optionally substituted aryl, optionally substituted aralkyl, optionally substituted heteroaryl, and optionally substituted heteroaralkyl;

X and Y are each independently chosen from $C(R^{10})(R^{11})$, $N(R^{12})$, O and S, wherein $R^{10}$ and $R^{11}$ are each independently selected from H, optionally substituted alkyl, optionally substituted aryl and optionally substituted heteroaryl; and $R^{12}$ is H, optionally substituted alkyl, optionally substituted aralkyl, optionally substituted heteroaralkyl, optionally substituted alkylcarbonyl, optionally substituted arylcarbonyl, optionally substituted heteroarylcarbonyl, optionally substituted aralkylcarbonyl, optionally substituted heteroaralkylcarbonyl, optionally substituted alkoxycarbonyl, optionally substituted aryloxycarbonyl, optionally substituted heteroaryloxycarbonyl, optionally substituted aralkyloxycarbonyl, or optionally substituted heteroaralkyloxycarbonyl;

including single stereoisomers and mixtures of stereoisomers thereof.

In another aspect, the invention relates to methods employing compounds represented by Formula II, or a pharmaceutically acceptable derivative or solvate thereof:

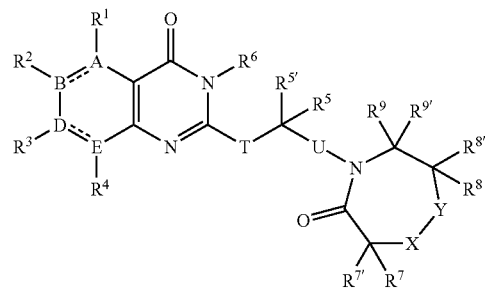

Formula II where:

T and U are independently a covalent bond, —C(O)—, or optionally substituted alkylene;

A, B, D and E are independently N, C, CH, O, S or absent, provided that:

no more than one of A, B, D or E is absent;

no more than two of A, B, D and E are —N=, and

A, B, D or E can be O or S only when one of A, B, D or E is absent; and

X, Y, $R^1$ to $R^9$ and $R^{5'}$, $R^{7'}$, $R^{8'}$ and $R^{9'}$ are as defined with regard to Formula I, provided that $R^1$, $R^2$, $R^3$ or $R^4$ is absent where A, B, D or E, respectively, is —N=, O, S or absent.

In a particularly preferred embodiment of Formula I and II, the stereogenic center to which $R^5$ and $R^{5'}$ are attached is of the R configuration.

The compounds encompassed by Formula II will be seen to include those of Formula I; they are likewise useful as active agents in the practice of the methods of treatment/inhibiting and in manufacture of compositions (including the pharmaceutical formulations) of the invention, and may also be useful as intermediates in the synthesis of such active agents. For the sake of simplicity in the following description and claims, substituents T, U, A, B, D and E will not be discussed in connection with certain compounds falling within the scope of Formula I.

Acyl refers to groups of from 1 to 8 carbon atoms of a straight, branched, or cyclic configuration or a combination thereof, attached to the parent structure through a carbonyl functionality. Such groups may be saturated or unsaturated, and aliphatic or aromatic. One or more carbons in the acyl residue may be replaced by oxygen (e.g., alkoxycarbonyl), nitrogen (e.g., carboxamido), or sulfur as long as the point of attachment to the parent remains at the carbonyl. Examples include acetyl-, benzoyl-, propionyl-, isobutyryl-, oxalyl-, t-butoxycarbonyl-, benzyloxycarbonyl, morpholinylcarbonyl, and the like. Lower-acyl refers to acyl groups containing one to five (particularly one to four) carbons.

Alkyl is intended to include linear, branched, or cyclic hydrocarbon structures and combinations thereof. Lower alkyl refers to alkyl groups of from 1 to 5 (particularly 1 to 4) carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like Alkylene is another subset of alkyl, referring to the same residues as alkyl, but having two points of attachment. Examples of alkylene include ethylene(—$CH_2CH_2$—), propylene(—$CH_2CH_2CH_2$—), dimethylpropylene(—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Alkoxy or alkoxyl refers to the group —O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to five (particularly one to four) carbons.

Amino refers to the group —$NH_2$. The term "substituted amino" refers to the group —NHR or —NRR where each R is independently selected from the group: optionally substituted alkyl-, optionally substituted alkoxy, optionally substituted aminocarbonyl-, optionally substituted aryl-, optionally substituted heteroaryl-, optionally substituted heterocyclyl-, acyl-, alkoxycarbonyl-, sulfanyl-, sulfinyl and sulfonyl-, e.g., diethylamino, methylsulfonylamino, furanyloxy-sulfonamino.

Aminocarbonyl- refers to the group —$NR^cCOR^b$, —$NR^cCO_2R^a$, or —$NR^cCONR^bR^c$, where $R^a$ is an optionally substituted $C_1$–$C_6$ alkyl-, aryl-, heteroaryl-, aryl-$C_1$–$C_4$ alkyl-, or heteroaryl-$C_1$–$C_4$ alkyl-group;

$R^b$ is H or optionally substituted $C_1$–$C_6$ alkyl-, aryl-, heteroaryl-, aryl-$C_1$–$C_4$ alkyl-, or heteroaryl-$C_1$–$C_4$ alkyl-group; and $R^c$ is hydrogen or $C_1$–$C_4$ alkyl-; and where each optionally substituted $R^b$ group is independently unsubstituted or substituted with one or more substituents independently selected from $C_1$–$C_4$ alkyl-, aryl-, heteroaryl-, aryl-$C_1$–$C_4$ alkyl-, heteroaryl-$C_1$–$C_4$ alkyl-, $C_1$–$C_4$ haloalkyl-, —$OC_1$–$C_4$ alkyl, —$OC_1$–$C_4$ alkylphenyl, —$C_1$–$C_4$ alkyl-OH, —$OC_1$–$C_4$ haloalkyl, halogen, —OH, —$NH_2$, —$C_1$–$C_4$ alkyl-$NH_2$, —$N(C_1$–$C_4$ alkyl)($C_1$–$C_4$ alkyl), —$NH(C_1$–$C_4$ alkyl), —$N(C_1$–$C_4$ alkyl)($C_1$–$C_4$ alkylphenyl), —$NH(C_1$–$C_4$ alkylphenyl), cyano, nitro, oxo (as a substitutent for heteroaryl), —$CO_2H$, —$C(O)OC_1$–$C_4$ alkyl, —$CON(C_1$–$C_4$ alkyl)($C_1$–$C_4$ alkyl), —$CONH(C_1$–$C_4$ alkyl), —$CONH_2$, —$NHC(O)(C_1$–$C_4$ alkyl), —$NHC(O)(phenyl)$, —$N(C_1$–$C_4$ alkyl)$C(O)(C_1$–$C_4$ alkyl), —$N(C_1$–$C_4$ alkyl)$C(O)(phenyl)$, —$C(O)C_1$–$C_4$ alkyl, —$C(O)C_1$–$C_4$ phenyl, —$C(O)C_1$–$C_4$ haloalkyl, —$OC(O)C_1$–$C_4$ alkyl, —$SO_2(C_1$–$C_4$ alkyl), —$SO_2(phenyl)$, —$SO_2(C_1$–$C_4$ haloalkyl), —$SO_2NH_2$, —$SO_2NH(C_1$–$C_4$ alkyl), —$SO_2NH(phenyl)$, —$NHSO_2(C_1$–$C_4$ alkyl), —$NHSO_2(phenyl)$, and —$NHSO_2(C_1$–$C_4$ haloalkyl).

Antimitotic refers to a drug for inhibiting or preventing mitosis, for example, by causing metaphase arrest. Some antitumour drugs block proliferation and are considered antimitotics.

Aryl and heteroaryl mean a 6-membered aromatic or a 5- or 6-membered heteroaromatic ring containing 0 or 1–4 heteroatoms, respectively, selected from O, N, or S; a bicyclic 9- or 10-membered aromatic or heteroaromatic ring system containing 0 or 1–4 (or more) heteroatoms, respectively, selected from O, N, or S; or a tricyclic 12- to 14-membered aromatic or heteroaromatic ring system containing 0 or 1–4 (or more) heteroatoms, respectively, selected from O, N, or S. The aromatic 6- to 14-membered carbocyclic rings include, e.g., phenyl, naphthyl, indanyl, tetralinyl, and fluorenyl and the 5- to 10-membered aromatic heterocyclic rings include, e.g., imidazole, pyridinyl, indolyl, thienyl, benzopyranonyl, thiazolyl, furanyl, benzimidazolyl, quinolinyl, isoquinolinyl, quinoxalinyl, pyrimidinyl, pyrazinyl, tetrazolyl and pyrazolyl.

Aralkyl refers to a residue in which an aryl moiety is attached to the parent structure via an alkyl residue. Examples include benzyl, phenethyl, phenylvinyl, phenylallyl and the like. Heteroaralkyl refers to a residue in which a heteroaryl moiety is attached to the parent structure via an alkyl residue. Examples include furanylmethyl, pyridinylmethyl, pyrimidinylethyl and the like.

Aralkoxy refers to the group aralkyl-O—. Similarly, heteroaralkoxy refers to the group heteroaralkyl-O—.

Carboxamido refers to the group —$CONR^bR^c$, where $R^b$ is H or optionally substituted $C_1$–$C_6$ alkyl-, aryl-, heteroaryl-, aryl-$C_1$–$C_4$ alkyl-, or heteroaryl-$C_1$–$C_4$ alkyl-group; and $R^c$ is hydrogen or $C_1$–$C_4$ alkyl-; and where each optionally substituted $R^b$ group is independently unsubstituted or substituted with one or more substituents independently selected from $C_1$–$C_4$ alkyl-, aryl-, heteroaryl-, aryl-$C_1$–$C_4$ alkyl-, heteroaryl-$C_1$–$C_4$ alkyl-, $C_1$–$C_4$ haloalkyl-, —$OC_1$–$C_4$ alkyl, —$OC_1$–$C_4$ alkylphenyl, —$C_1$–$C_4$ alkyl-OH, —$OC_1$–$C_4$ haloalkyl, halogen, —OH, —$NH_2$, —$C_1$–$C_4$ alkyl-$NH_2$, —$N(C_1$–$C_4$ alkyl)($C_1$–$C_4$ alkyl), —$NH(C_1$–$C_4$ alkyl), —$N(C_1$–$C_4$ alkyl)($C_1$–$C_4$ alkylphenyl), —$NH(C_1$–$C_4$ alkylphenyl), cyano, nitro, oxo (as a substitutent for heteroaryl), —$CO_2H$, —$C(O)OC_1$–$C_4$ alkyl, —$CON(C_1$–$C_4$ alkyl)($C_1$–$C_4$ alkyl), —$CONH(C_1$–$C_4$ alkyl), —$CONH_2$, —$NHC(O)(C_1$–$C_4$ alkyl), —$NHC(O)(phenyl)$, —$N(C_1$–$C_4$ alkyl)$C(O)(C_1$–$C_4$ alkyl), —$N(C_1$–$C_4$ alkyl)$C(O)(phenyl)$, —$C(O)C_1$–$C_4$ alkyl, —$C(O)C_1$–$C_4$ phenyl, —$C(O)C_1$–$C_4$ haloalkyl, —$OC(O)C_1$–$C_4$ alkyl, —$SO_2(C_1$–$C_4$ alkyl), —$SO_2(phenyl)$, —$SO_2(C_1$–$C_4$ haloalkyl), —$SO_2NH_2$, —$SO_2NH(C_1$–$C_4$ alkyl), —$SO_2NH(phenyl)$, —$NHSO_2(C_1$–$C_4$ alkyl), —$NHSO_2(phenyl)$, and —$NHSO_2(C_1$–$C_4$ haloalkyl). Carboxamido is meant to include carbamoyl-; lower-alkyl carbamoyl-; benzylcarbamoyl-; phenylcarbamoyl-; methoxymethyl-carbamoyl-; and the like.

Halogen or halo refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

Heterocyclyl means a cycloalkyl or aryl residue in which one to four of the carbons is replaced by a heteroatom such as oxygen, nitrogen or sulfur. Examples of heterocycles that fall within the scope of the invention include imidazolinyl, pyrrolidinyl; pyrazolyl, pyrrolyl, indolyl, quinolinyl, isoquinolinyl, tetrahydroisoquinolinyl, benzofuranyl, benzodioxanyl, benzodioxyl (commonly referred to as methylenedioxyphenyl, when occurring as a substituent), tetrazolyl, morpholinyl, thiazolyl, pyridinyl, pyridazinyl, piperidinyl, pyrimidinyl, thienyl, furanyl, oxazolyl, oxazolinyl, isoxazolyl, dioxanyl, tetrahydrofuranyl and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

It will be understood that when a group or moiety is "optionally substituted," the group or moiety may be unsubstituted or may be substituted by one or more of the substituents defined herein, where each substituent is selected independently. It will be further understood by those skilled in the art with respect to any groups containing one or more substituents that such groups are not intended to introduce any substituent or substitution patterns that are sterically impractical and/or synthetically non-feasible and/or inherently unstable.

Substituted alkoxy refers to the group —O-(substituted alkyl).

Substituted-alkyl, aryl, and heteroaryl, which includes the substituted alkyl, aryl and heteroaryl moieties of any group containing an optionally substituted alkyl, aryl and heteroaryl moiety (e.g., alkoxy, aralkyl and heteroaralkyl), refer respectively to alkyl, aryl, and heteroaryl wherein one or more (up to about 5, preferably up to about 3) hydrogen atoms are replaced by a substituent, wherein each substituent is independently selected from the group:

—$R^a$, —$OR^b$, —$O(C_1$–$C_2$ alkyl)O— (as an aryl substituent), —$SR^b$, —$NR^bR^c$, —$C(=NR^c)$—$NR^bR^c$, halogen, cyano, nitro, —$COR^b$, —$CO_2R^b$, —$CONR^bR^c$, —$OCOR^b$, —$OCO_2R^b$, —$OCONR^bR^c$, —$NR^cCOR^b$, —$NR^cCO_2R^b$— $NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is an optionally substituted $C_1$–$C_6$ alkyl, aryl, heteroaryl, aryl-$C_1$–$C_4$ alkyl-, or heteroaryl-$C_1$–$C_4$ alkyl-group, $R^b$ is H or optionally substituted $C_1$–$C_6$ alkyl, aryl, heteroaryl, aryl-$C_1$–$C_4$ alkyl-, or heteroaryl-$C_1$–$C_4$ alkyl-group;

$R^c$ is hydrogen or $C_1$–$C_4$ alkyl;

where each optionally substituted $R^a$ group and $R^b$ group is independently unsubstituted or substituted with one or more substituents independently selected from $C_1$–$C_4$ alkyl, aryl, heteroaryl, aryl-$C_1$–$C_4$ alkyl-, heteroaryl-$C_1$–$C_4$ alkyl-, $C_1$–$C_4$ haloalkyl, —$OC_1$–$C_4$ alkyl, —$OC_1$–$C_4$ alkylphenyl, —$C_1$–$C_4$ alkyl-OH, —$OC_1$–$C_4$ haloalkyl, halogen, —OH, —$NH_2$, —$C_1$–$C_4$ alkyl-$NH_2$, —$N(C_1$–$C_4$ alkyl)($C_1$–$C_4$ alkyl), —$NH(C_1$–$C_4$ alkyl), —$N(C_1$–$C_4$ alkyl)($C_1$–$C_4$ alkylphenyl), —$NH(C_1$–$C_4$ alkylphenyl), cyano, nitro, oxo (as a substitutent for heteroaryl), —$CO_2H$, —$C(O)OC_1$–$C_4$ alkyl, —$CON(C_1$–$C_4$ alkyl)($C_1$–$C_4$ alkyl), —$CONH(C_1$–$C_4$ alkyl), —$CONH_2$, —$NHC(O)(C_1$–$C_4$ alkyl), —$NHC(O)(phenyl)$, —$N(C_1$–$C_4$ alkyl)C(O)($C_1$–$C_4$ alkyl), —$N(C_1$–$C_4$ alkyl)C(O)(phenyl), —$C(O)C_1$–$C_4$ alkyl, —$C(O)C_1$–$C_4$ phenyl, —$C(O)C_1$–$C_4$ haloalkyl, —$OC(O)C_1$–$C_4$ alkyl, —$SO_2(C_1$–$C_4$ alkyl), —$SO_2(phenyl)$, —$SO_2(C_1$–$C_4$ haloalkyl), —$SO_2NH_2$, —$SO_2NH(C_1$–$C_4$ alkyl), —$SO_2NH(phenyl)$, —$NHSO_2(C_1$–$C_4$ alkyl), —$NHSO_2(phenyl)$, and —$NHSO_2(C_1$–$C_4$ haloalkyl).

In the compounds of Formula II where T and/or U are substituted alkylene, the term "substituted" also refers to alkylene groups where one or more (up to 3, particularly 1) carbon atoms are replaced by a heteroatom independently selected from O, N, or S, such as —$CH_2$—S—$CH_2$—.

Sulfanyl refers to the groups: —S-(optionally substituted alkyl), —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), —S(O)-(optionally substituted heterocyclyl); and —S(O)-(optionally substituted amino).

Sulfonyl refers to the groups: —$S(O_2)$—H, —$S(O_2)$-(optionally substituted alkyl), —$S(O_2)$-optionally substituted aryl), —$S(O_2)$-(optionally substituted heteroaryl), —$S(O_2)$-(optionally substituted heterocyclyl), —$S(O_2)$-(optionally substituted alkoxy), —$S(O_2)$-optionally substituted aryloxy), —$S(O_2)$-(optionally substituted heteroaryloxy), —$S(O_2)$-(optionally substituted heterocyclyloxy); and —$S(O_2)$-(optionally substituted amino).

Pharmaceutically acceptable derivatives of Formula I or II include any pharmaceutically acceptable salt, ester, or salt of such ester, of a compound of Formula I or II which, upon administration to the recipient is capable of providing (directly or indirectly) a compound of Formula I or II or an active metabolite or residue thereof. For simplicity, in certain instances herein reference is made specifically to salts of a compound of Formula I or II. It is appreciated that other pharmaceutically acceptable derivatives, such as esters, of a compound of Formula I or II are also suitable for use in the present invention in the manner specifically disclosed for salts, as though expressly set forth herein.

Pharmaceutically acceptable acid addition salt refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Solvate refers to the compound formed by the interaction of a solvent and a compound of Formula I or II or a pharmaceutically acceptable derivative thereof. Suitable solvates are those formed with pharmaceutically acceptable solvents, including hydrates (i.e., wherein the solvent is water). It will be understood that phrases such as "a compound of Formula I or II or a pharmaceutically acceptable derivative (e.g., salt) or solvate thereof" are intended to encompass the compound of Formula I or II, a pharmaceutically acceptable derivative (e.g., salt) of the compound, a solvate of the compound and a solvate of a pharmaceutically acceptable derivative (e.g., salt) of the compound.

Many of the compounds described herein contain one or more asymmetric centers (e.g. the carbon to which $R^5$ and $R^{5'}$ are attached) and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

When desired, the R- and S-isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

In one embodiment of Formula II, A, B, D and E are independently chosen from —C= and —N=, and in a particular embodiment each is —C=.

In one embodiment of Formula II, T is optionally substituted C1–C4 alkylene or is a covalent bond (i.e., absent). Where T is alkylene having a carbon substituted by a heteroatom, the heteroatom is not bound directly to the bicylic structure. In other embodiments, T is aminoalkylene or amidoalkylene. In other embodiments, T is a covalent bond, alkylene, or alkylene substituted with halo or oxo.

In one embodiment of Formula II, U is optionally substituted C1–C4 alkylene or is a covalent bond. Where U is alkylene having a carbon substituted by a heteroatom, the heteroatom is not bound directly to the diazepinone structure comprising X and Y. In other embodiments, U is aminoalkylene or amidoalkylene. In other embodiments, U is a covalent bond, alkylene, or alkylene substituted with halo or oxo.

In one embodiment of the compounds of Formula I and II, $R^1$, $R^2$, $R^3$ and $R^4$ are each independently selected from H, halogen, cyano, optionally substituted $C_1$–$C_4$ alkyl, $C_1$–$C_4$ haloalkyl, optionally substituted $C_1$–$C_4$ alkoxy, and. $C_1$–$C_4$ haloalkoxy. In another embodiment, $R^1$, $R^2$, $R^3$ and $R^4$ are each independently selected from H, halogen, and cyano. In yet another embodiment, $R^1$, $R^2$, $R^3$ and $R^4$ are each independently selected from H and halogen. In specific embodiments of the compounds of Formula I and II, $R^1$, $R^2$ and $R^4$ are each H and $R^3$ is halogen, specifically, chloro.

In another embodiment of the compounds of Formula I and II, $R^5$ and $R^{5'}$ are each independently selected from H and $C_1$–$C_4$ alkyl. In another embodiment, $R^{5'}$ is H and $R^5$ is $C_1$–$C_4$ alkyl. In specific embodiments of the compounds of Formula I and II, $R^{5'}$ is H and $R^5$ is H, ethyl, cyclopropyl, iso-propyl, or t-butyl, more particularly ethyl, cyclopropyl, or iso-propyl and most particularly iso-propyl.

In another embodiment, $R^5$ and $R^{5'}$ taken together form a 3–7 membered carbocyclic ring, in which one or more of the ring hydrogens may optionally be substituted with one or more of the following groups: hydroxyl, halogen (particularly chloro and fluoro), optionally substituted $C_{1-4}$ alkyl-(particularly methyl), and optionally substituted $C_{1-4}$ alkoxy (particularly methoxy), cyano, amino, substituted amino, or carbamyl.

In yet another embodiment of the compounds of Formula I and II, $R^6$ is optionally substituted $C_1$–$C_8$ alkyl, optionally substituted aryl-$C_1$–$C_4$ alkyl- or optionally substituted heteroaryl-$C_1$–$C_4$ alkyl-. In another embodiment, $R^6$ is optionally substituted phenyl-$C_1$–$C_4$ alkyl-, preferably, $R^6$ is optionally substituted benzyl. In specific embodiments of the compounds of Formula I and II, $R^{6'}$ is benzyl.

In a further embodiment of the compounds of Formula I and II, $R^7$, $R^{7'}$, $R^8$, $R^{8'}$, $R^9$ and $R^{9'}$ are each independently selected from H and $C_1$–$C_4$ alkyl. In another embodiment, $R^9$ and $R^{9'}$ are each H and $R^7$ and $R^{7'}$ or $R^8$ and $R^{8'}$ are each independently H or $C_1$–$C_4$ alkyl. In specific embodiments, $R^7$, $R^{7'}$, $R^8$, $R^{8'}$, $R^9$, and $R^{9'}$ are each H; or $R^7$, $R^{7'}$, $R^9$, and $R^{9'}$ are each H and $R^8$ and $R^{8'}$ are each H or $C_1$–$C_4$ alkyl, specifically methyl; or $R^8$, $R^{8'}$, $R^9$, and $R^{9'}$ are each H and $R^7$ and $R^{7'}$ are each H or $C_1$–$C_4$ alkyl, specifically methyl.

In yet another embodiment of the compounds of Formula I and II, one of X or Y is $C(R^{10})(R^{11})$, wherein $R^{10}$ and $R^{11}$ are each independently selected from H or $C_1$–$C_4$ alkyl, and the other of X or Y is $N(R^{12})$, where $R^{12}$ is H, $C_1$–$C_4$ alkyl, optionally substituted aralkyl, optionally substituted heteroaralkyl, $C_1$–$C_6$ alkylcarbonyl, optionally substituted arylcarbonyl, optionally substituted heteroarylcarbonyl, optionally substituted aralkylcarbonyl, optionally substituted heteroaralkylcarbonyl, $C_1$–$C_6$ alkoxycarbonyl, optionally substituted aryloxycarbonyl, optionally substituted heteroaryloxycarbonyl, optionally substituted aralkyloxycarbonyl, optionally substituted heteroaralkyloxycarbonyl, where the optionally substituted aryl or heteroaryl groups or moieties are unsubstituted or substituted with one or more substituents selected from $C_1$–$C_4$ alkyl, $C_1$–$C_4$ haloalkyl, $C_1$–$C_4$ alkoxy, $C_1$–$C_4$ haloalkoxy, amino, $C_1$–$C_4$ alkylamino, di-$C_1$–$C_4$ alkylamino, carboxy, $C_1$–$C_4$ alkylcarbonyloxy, $C_1$–$C_4$ alkoxycarbonyl, carboxamido, $C_1$–$C_4$ alkylcarboxamido, aminocarbonyl, $C_1$–$C_4$ alkylaminocarbonyl, di-$C_1$–$C_4$ alkylaminocarbonyl, cyano, $C_1$–$C_4$ alkylcarbonyl, halogen, hydroxyl, mercapto and nitro. In another embodiment, X is $C(R^{10})(R^{11})$, wherein $R^{10}$ and $R^{11}$ are each H or $C_1$–$C_4$ alkyl, and Y is $N(R^{12})$, where $R^{12}$ is H, $C_1$–$C_4$ alkyl, aralkyl, heteroaralkyl, $C_1$–$C_6$ alkylcarbonyl, arylcarbonyl, heteroarylcarbonyl. In specific embodiments of the compounds of Formula I and II, X is $CH_2$, and Y is $N(R^{12})$, where $R^{12}$ is H, methyl, benzyl or acetyl (—C(O)methyl).

As will be appreciated by those skilled in the art, the compounds described herein possess a potentially chiral center at the carbon to which $R^5$, $R^7$, $R^8$, and $R^9$ is attached. Thus, for example, the $R^5$ position may comprise two substitution groups, $R^5$ and $R^{5'}$. The $R^5$ and $R^{5'}$ groups may be the same or different; if different, the compound is chiral.

When the $R^5$ and $R^{5'}$ groups are different, preferred embodiments utilize only a single non-hydrogen $R^5$. The invention contemplates the use of pure enantiomers and mixtures of enantiomers, including racemic mixtures, although the use of the substantially optically pure enantiomer will generally be preferred. In the compounds of Formula I and II, the stereogenic center to which $R^5$ and $R^{5'}$ are attached is preferably of the R configuration.

Similarly, the $R^7$, $R^8$ and $R^9$ position may comprise two substitution groups, $R^7$ and $R^{7'}$, $R^8$ and $R^{8'}$, and $R^9$ and $R^{9'}$, respectively. The $R^7$ and $R^{7'}R^8$ and $R^{8'}$, or $R^9$ and $R^{9'}$ groups may be the same or different; if different, the compound is chiral. When the $R^7$ and $R^{7'}$, $R^8$ and $R^{8'}$, or $R^9$ and $R^{9'}$ groups are different, preferred embodiments utilize only a single non-hydrogen $R^7$, $R^8$ or $R^9$. The invention contemplates the use of pure enantiomers and mixtures of enantiomers, including racemic mixtures, although the use of the substantially optically pure enantiomer will generally be preferred.

In one of its particular aspects the present invention pertains to a compound represented by Formula I or II, having a substituent selected from one or more of the following for $R^1$ to $R^9$, $R^{5'}$, $R^{7'}$, $R^{8'}$, $R^{9'}$, T, U, X, Y, A, B, D and E:

$R^1$, $R^2$, $R^3$ and $R^4$ are independently chosen from hydrogen, halo (particularly chloro and fluoro), lower alkyl (particularly methyl), substituted lower alkyl, lower alkoxy (particularly methoxy), and cyano;

$R^6$ is aralkyl or substituted arlalkyl (particularly benzyl or substituted benzyl; most particularly benzyl);

$R^5$ is $C_3$ to $C_5$ alkyl (particularly iso-propyl, c-propyl, or t-butyl);

$R^{5'}$ is hydrogen;

$R^7$, $R^{7'}$, $R^8$, $R^{8'}$, $R^9$ and $R^{9'}$ are each independently selected from H and $C_1$–$C_4$ alkyl (particularly methyl) (more particularly, $R^9$ and $R^{9'}$ are each H and $R^7$ and $R^{7'}$ or $R^8$ and $R^{8'}$ are each independently H or $C_1$–$C_4$ alkyl, particularly methyl);

X is $C(R^{10})(R^{11})$, wherein $R^{10}$ and $R^{11}$ are each H or $C_1$–$C_4$ alkyl (particularly each H);

Y is $N(R^{12})$, where $R^{12}$ is H, $C_1$–$C_4$ alkyl, aralkyl, heteroaralkyl, $C_1$–$C_6$ alkylcarbonyl, arylcarbonyl, heteroarylcarbonyl (particularly H, methyl, benzyl or acetyl (—C(O) methyl));

one or both of T and U is a covalent bond (particularly both); and

A, B, D and E are each —C═.

Compounds illustrated by the above described groupings and subgroups, individually or combined together, are particularly suitable for practice of the present invention.

The compounds of the invention may be prepared as shown in the General Methods and as described below, utilizing techniques well known in the art. The starting materials for the schemes shown in the figures are commercially available, e.g., from Aldrich Chemical Company, Milwaukee, Wis. or may be readily prepared by those skilled in the art using commonly employed synthetic methodology.

The derivatives and solvates of the compounds mentioned herein may as required be produced by methods conventional in the art. For example, if an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine; as well as inorganic salts derived from sodium, calcium, potassium, magnesium, manganese, iron, copper, zinc, aluminum, and lithium.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Once made, the compounds of the invention find use in a variety of applications. As will be appreciated by those skilled in the art, mitosis may be altered in, a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compounds of the invention are used to modulate, particularly inhibit, mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to and/or modulate, particularly inhibit, the activity of a mitotic kinesin, KSP. In a preferred embodiment, the KSP is human KSP, although KSP kinesins from other organisms may also be used. In this context, inhibit means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. Pat. Nos. 6,414,121 and 6,437,115, hereby incorporated by reference in their entirety. In addition, other mitotic kinesins may be used in the present invention. However, the compounds of the invention have been shown to have specificity for KSP.

For assay of activity, generally either KSP or a compound according to the invention is non-diffusably bound to an insoluble support having isolated sample receiving areas (e.g., a microtiter plate, an array, etc.). The insoluble support may be made of any composition to which the compounds can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the compound is not crucial so long as it is compatible with the reagents and overall methods of the invention, maintains the activity of the compound and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

The antimitotic agents of the invention may be used on their own to modulate the activity of a mitotic kinesin, particularly KSP. In this embodiment, the antimitotic agents of the invention are combined with KSP and the activity of KSP is assayed. Kinesin activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes; such as kinases or proteases; and specific kinesin cellular activities such as spindle pole separation.

Methods of performing motility assays are well known to those of skill in the art. (See e.g., Hall, et al. (1996), Biophys. J., 71: 3467–3476, Turner et al., 1996, AnaL Biochem. 242 (1):20–5; Gittes et al., 1996, Biophys. J. 70(I): 418–29; Shirakawa et al., 1995, J. Exp. BioL 198:1809–15; Winkelmann et al., 1995, Biophys. J. 68: 2444–53; Winkelmann et al., 1995, Biophys. J. 68: 72S.)

Methods known in the art for determining ATPase hydrolysis activity also can be used. Preferably, solution based assays are utilized. U.S. application Ser. No. 09/314, 464, filed May 18, 1999 (U.S. Pat. No. 6,410,254), hereby incorporated by reference in its entirety, describes such assays. Alternatively, conventional methods are used. For example, $P_i$ release from kinesin can be quantified. In one preferred embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 µL of reaction is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10–15 minutes and the plate is read at an absorbance of 650 nm. If phosphate standards were used, absorbance readings can be converted to mM $P_1$ and plotted over time. Additionally, ATPase assays known in the art include the luciferase assay.

ATPase activity of kinesin motor domains also can be used to monitor the effects of modulating agents. In one embodiment ATPase assays of kinesin are performed in the absence of microtubules. In another embodiment, the ATPase assays are performed in the presence of microtubules. Different types of modulating agents can be detected in the above assays. In a preferred embodiment, the effect of a modulating agent is independent of the concentration of microtubules and ATP. In another embodiment, the effect of the agents on kinesin ATPase can be decreased by increasing the concentrations of ATP, microtubules or both. In yet another embodiment, the effect of the modulating agent is increased by increasing concentrations of ATP, microtubules or both.

Agents that modulate the biochemical activity of KSP in vitro may then be screened in vivo. Methods for such agents in vivo include assays of cell cycle distribution, cell viability, or the presence, morphology, activity, distribution, or amount of mitotic spindles. Methods for monitoring cell cycle distribution of a cell population, for example, by flow cytometry, are well known to those skilled in the art, as are methods for determining cell viability. See for example, U.S. patent application "Methods of Screening for Modulators of Cell Proliferation and Methods of Diagnosing Cell Proliferation States," filed Oct. 22, 1999, Ser. No. 09/428,156, hereby incorporated by reference in its entirety.

In addition to the assays described above, microscopic methods for monitoring spindle formation and malformation are well known to those of skill in the art (see, e.g., Whitehead and Rattner (1998), J. Cell Sci. 111:2551–61; Galgio et al, (1996) J. Cell biol., 135:399–414).

The compounds of the invention inhibit the KSP kinesin. One measure of inhibition is $IC_{50}$, defined as the concentration of the compound at which the activity of KSP is decreased by fifty percent relative to a control. Preferred compounds have $IC_{50}$'s of less than about 1 mM, with preferred embodiments having $IC_{50}$'s of less than about 100 µM, with more preferred embodiments having $IC_{50}$'s of less than about 10 µM, with particularly preferred embodiments having $IC_{50}$'s of less than about 1 µM, and especially preferred embodiments having $IC_{50}$'s of less than about 100 nM, and with the most preferred embodiments having $IC_{50}$'s of less than about 10 nM. Measurement of $IC_{50}$ is done using an ATPase assay.

Another measure of inhibition is $K_I$. For compounds with $IC_{50}$'s less than 1 µM, the $K_i$ or $K_d$ is defined as the dissociation rate constant for the interaction of the compounds described herein with KSP. Preferred compounds have $K_i$'s of less than about 100 µM, with preferred embodiments having $K_i$'s of less than about 10 µM, and particularly preferred embodiments having $K_i$'s of less than about 1 µM and especially preferred embodiments having $K_i$'s of less than about 100 nM, and with the most preferred embodiments having $K_i$'s of less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Preferred compounds have $GI_{50}$'s of less than about 1 mM. The level of preferability of embodiments is a function of their $GI_{50}$ : those having $GI_{50}$'s of less than about 20 µM are more preferred; those having $GI_{50}$'s of 10 µM more so; those having $GI_{50}$ of less than about 1 μM more so; those having $GI_{50}$'s of 100 nM more so; those having $GI_{50}$ of less than about 10 nM even more so. Measurement of $GI_{50}$ is done using a cell proliferation assay.

The compound and compositions of the invention are used to treat cellular proliferation diseases. Disease states which can be treated by the methods, compounds and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in one embodiment, the invention herein includes application to cells or individuals afflicted or subject to impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma; lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis); brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, the compounds or compositions of the invention are administered to cells. By "administered" herein is meant administration of a therapeutically effective dose of the antimitotic agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered.

A "patient" for the purpose of the present invention includes both humans and other animals, particularly mammals, and other organisms. Thus the methods are applicable to both human therapy and veterinary applications. In the preferred embodiment the patient is a mammal, and in the most preferred embodiment the patient is human.

Anti-mitotic agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–99.9 wt. %. The compounds of Formula I and II, and the pharmaceutically acceptable derivatives and solvates thereof can be administered alone or in combination with other treatments, i.e., radiation, or other therapeutic agents, such as the taxane class of agents that appear to act on microtubule formation or the camptothecin class of topoisomerase I inhibitors. When so-used, other therapeutic agents can be administered before, concurrently (whether in separate dosage forms or in a combined dosage form), or after administration of an active agent of the present invention.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Pharmaceutical formulations include a compound of Formula I or II or a pharmaceutically acceptable derivative or solvate thereof, and one or more pharmaceutically acceptable excipients. As is known in the art, pharmaceutical excipients are secondary ingredients that function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them. Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995). The concentration of a therapeutically active agent in a formulation can vary widely, from about 0.1 to 99.9 wt. %, depending on the nature of the formulation.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colorants, flavorants, sweetening agents, polymers, waxes or other solubility-modulating materials.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:

alcohol, e.g., 5% alcohol (e.g., in dextrose and water ("DMW") or DMW in normal saline solution ("NSS"), including in 5% dextrose and water ("D5/W"), or D5/W in NSS);

synthetic amino acid such as Aminosyn, FreAmine, Travasol, e.g., 3.5 or 7; 8.5; 3.5, 5.5 or 8.5% respectively;

ammonium chloride e.g., 2.14%;

dextran 40, in NSS e.g., 10% or in D5/W e.g., 10%;

dextran 70, in NSS e.g., 6% or in D5/W e.g., 6%;

dextrose (glucose, D5/W) e.g., 2.5–50%;

dextrose and sodium chloride e.g., 5–20% dextrose and 0.22–0.9% NaCl;

lactated Ringer's (Hartmann's) e.g., NaCl 0.6%, KCl 0.03%, $CaCl_2$ 0.02%;

lactate 0.3%;

mannitol e.g., 5%, optionally in combination with dextrose e.g., 10% or NaCl e.g., 15 or 20%;

multiple electrolyte solutions with varying combinations of electrolytes, dextrose, fructose, invert sugar Ringer's e.g., NaCl 0.86%, KCl 0.03%, $CaCl_2$ 0.033%;

sodium bicarbonate e.g., 5%;

sodium chloride e.g., 0.45, 0.9, 3, or 5%;

sodium lactate e.g., ⅙ M; and sterile water for injection

The pH of such IV fluids may vary, and will typically be from 3.5 to 8 as known in the art.

The administration of the antimitotic agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the anti-mitotic agents may be directly applied as a solution or spray.

Yet another aspect of the invention relates to a kit comprising a compound of Formula I or II, or a pharmaceutically acceptable derivative or solvate thereof, and a package insert or other labeling including directions for treating a cellular proliferative disease by administering an effective amount of the compound, derivative or solvate. In one particular such aspect, the compound, derivative or solvate is provided as a pharmaceutical composition.

To employ the compounds of the invention in a method of screening for compounds that bind to KSP kinesin, the KSP is bound to a support, and a compound of the invention (which is an anti mitotic agent) is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the anti-mitotic agent to KSP may be done in a number of ways. In a preferred embodiment, the anti-mitotic agent (the compound of the invention) is labeled, for example, with a fluorescent or radioactive moiety and binding determined directly. For example, this may be done by attaching all or a portion of KSP to a solid support, adding a labeled anti-mitotic agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions-using $^{125}$I, or with fluorophores. Alternatively, more than one component may be labeled with different labels; using $^{125}$I for the proteins, for example, and a fluorophor for the anti-mitotic agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional-groups. -Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produce. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays may be done by combining KSP and a drug candidate in a first sample. A second sample comprises a mitotic agent, KSP and a drug candidate. This may be performed in either the presence or absence of microtubules. The binding of the drug candidate is determined for both samples, and a change, or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a preferred embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature, which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the antimitotic agent, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein.

The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

General Methods

The compounds of this invention were prepared according to the general process outlined in Scheme 1A, Scheme 1B, Scheme 2, Scheme 3 and/or-Scheme 3a and described in Examples 1 to 8 below.

Reductive amination of the primary amino group in the quinazolinone 1 with (2-oxo-ethyl)-carbamic acid tert-butyl ester gave the corresponding secondary amine. Acylation with either acryloyl chloride or chloropivaloyl chloride followed by deprotection of the tertiary amide and base mediated cyclisation gave the desired diazepanones. If desired, further functionalization of the basic amine could be accomplished under conditions well known to those skilled in the art (Scheme 1A and Scheme 1B).

Scheme 1A

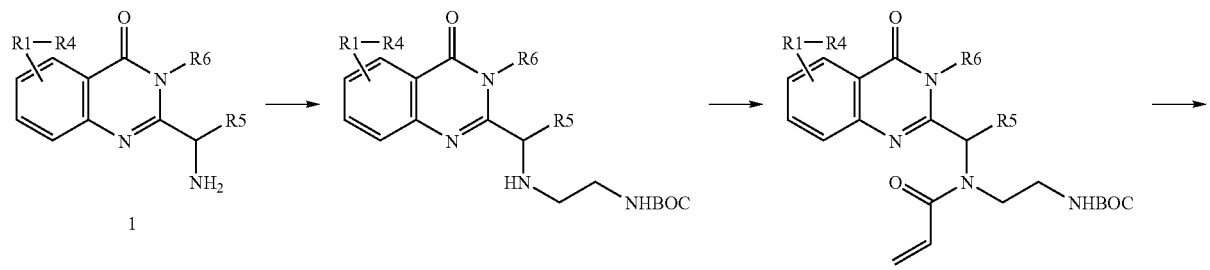

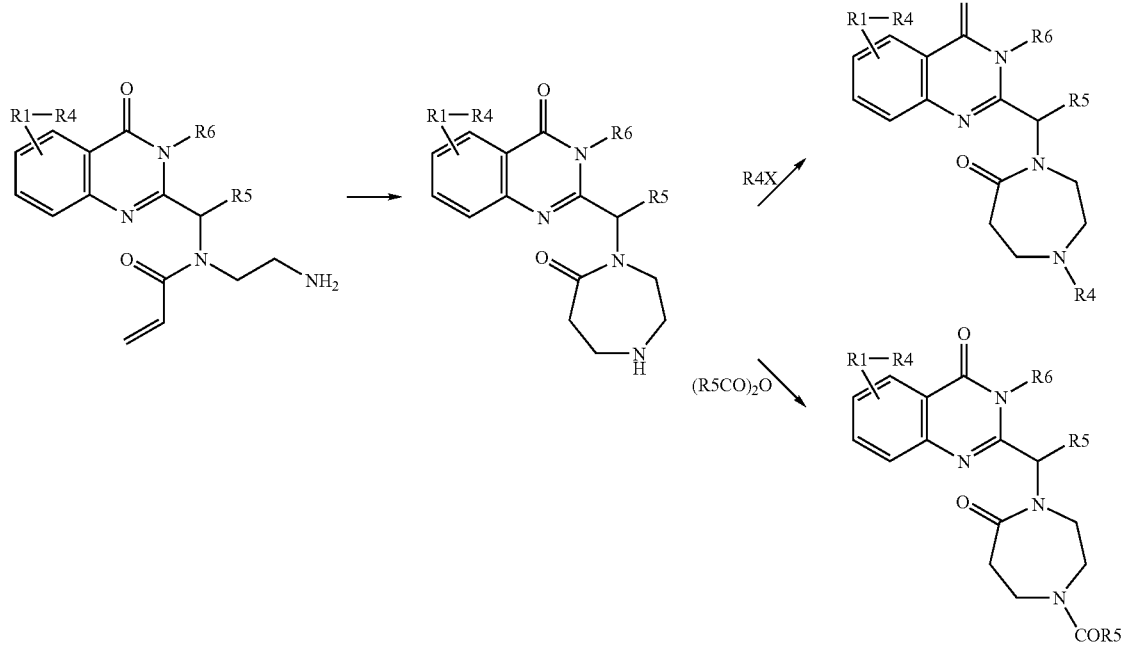

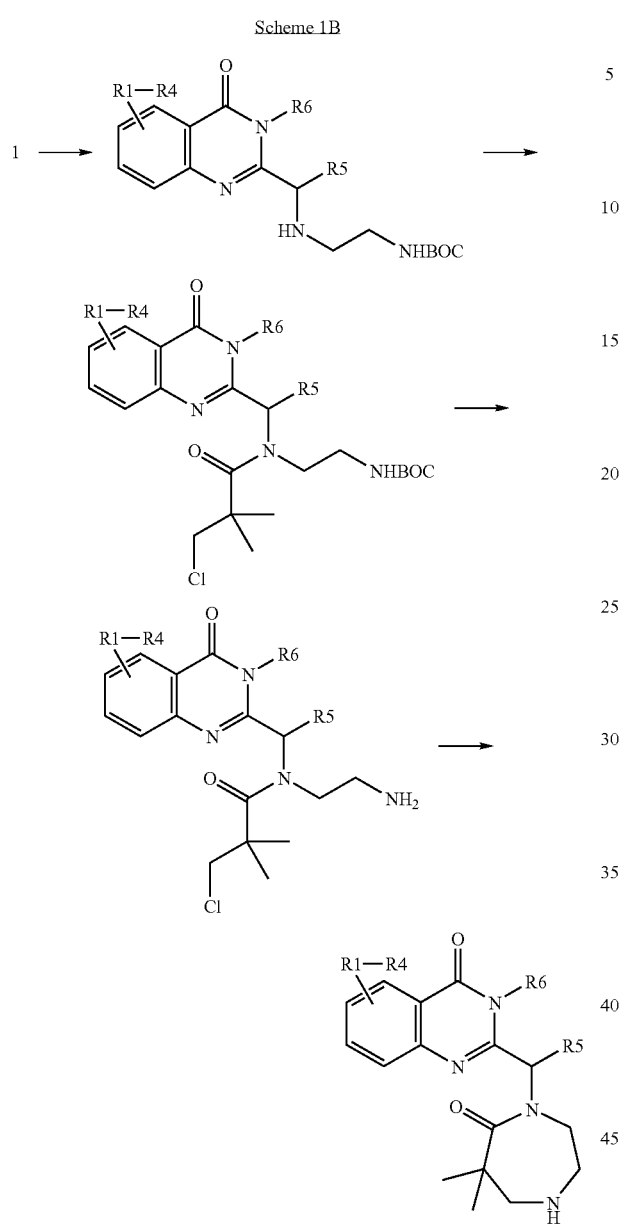

In an alternative method (Scheme 2), displacement of the bromide in quinazolinone 2 with (2-amino-ethyl)-carbamic acid tert-butyl ester followed by acylation with acryolyl chloride and cyclisation also gave the required diazepanone.

Scheme 2

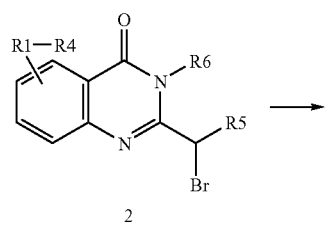

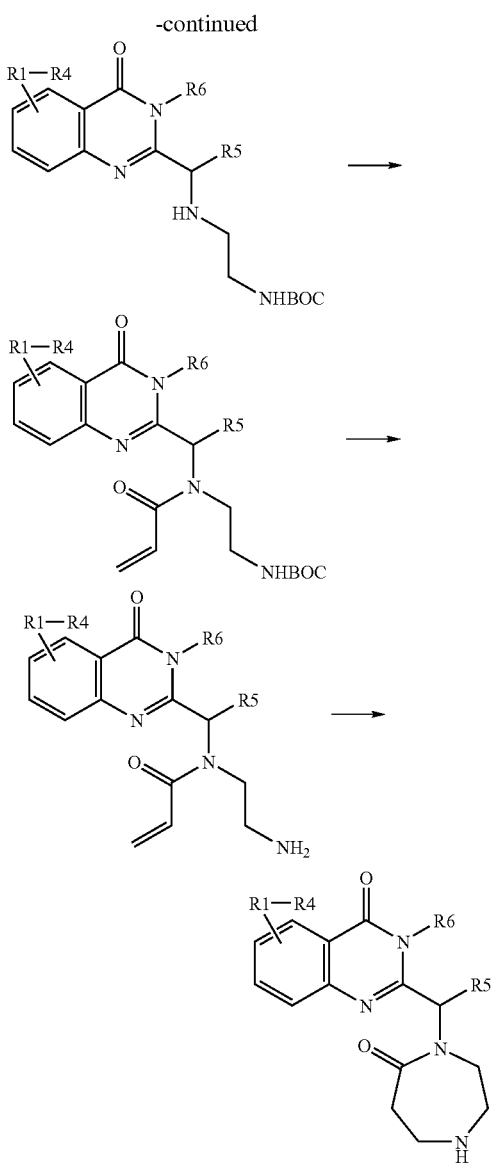

Scheme 3 illustrates the synthesis of compounds of Formula II wherein A=B=D=carbon, $R^1=R^2=R^3$=hydrogen, E=nitrogen, $R^4$ is absent, $R^6$ is benzyl, $R^5$ is isopropyl, $R^{5'}$ is hydrogen, T=U=bond, X=$CH_2$, Y=NH, and $R^7=R^{7'}=R^8=R^{8'}=R^9=R^{9'}$=hydrogen. The synthesis of Intermediate 1 is described in U.S. patent application Ser. No. 10/444,283 and PCT/US03/16500, each filed May 22, 2003, incorporated herein by reference in their entirety. Compounds of Formula II can be prepared according to Scheme 3 utilizing analogous starting materials such as described in those patent applications.

Scheme 3

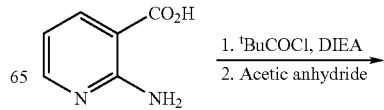

-continued

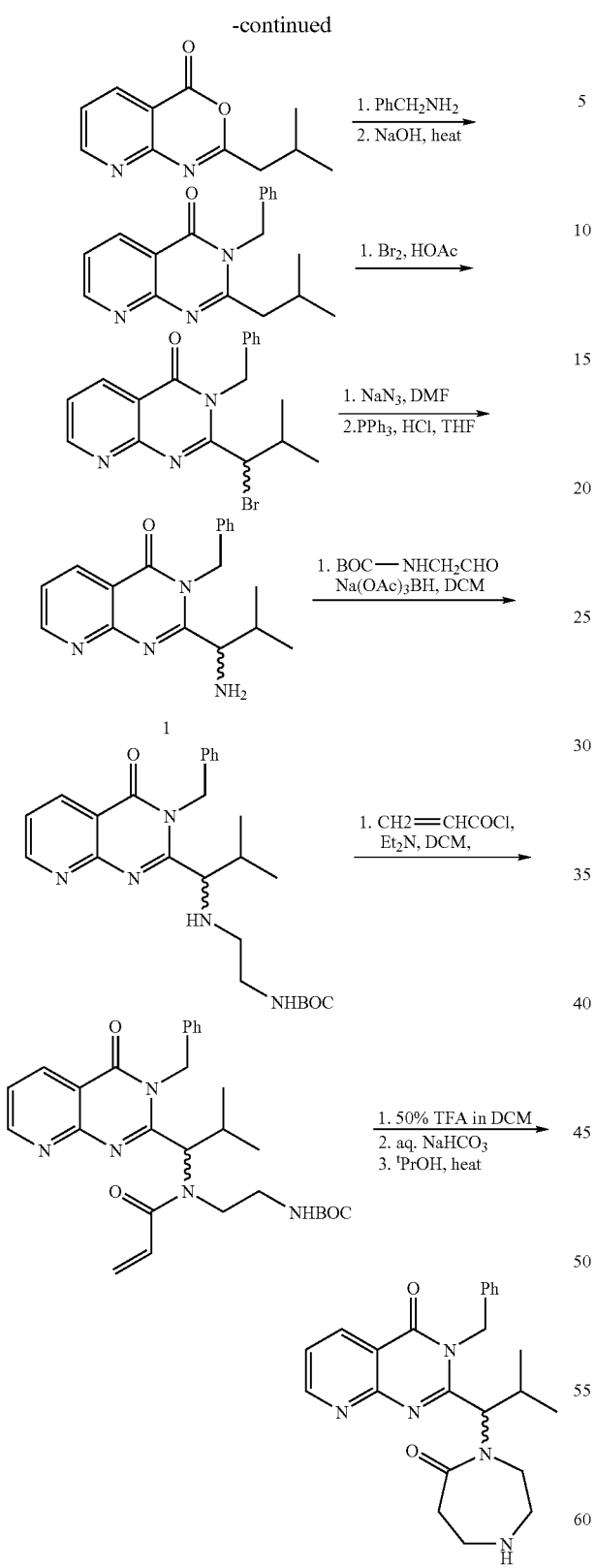

Intermediate 1 and analogs thereof useful herein can be prepared according to Scheme 3a starting with optionally substituted amino-nicotinic acid, amino-isonicotinic acid, amino-pyridine-carboxylic acid, amino-pyrazine-carboxylic acid, amino-pyridazine-carboxylic acid and amino-pyrimidine-carboxylic acids of Formula 101 (U.S. patent application Ser. No. 10/444,283 and PCT/US03/16500). These and other reactants are commercially available, e.g., from Aldrich Chemical Company, Milwaukee, Wis. or may be readily prepared by those skilled in the art using commonly employed synthetic methodology. In Scheme 3a, $R^1$–$R^4$, W, X, Y, Z, $R^6$, $R^{6'}$, and $R^5$ are selected to correspond respectively to the desired $R^1$–$R^4$, A, B, D, E, $R^5$, $R^{5'}$ and $R^6$ of Formula II.

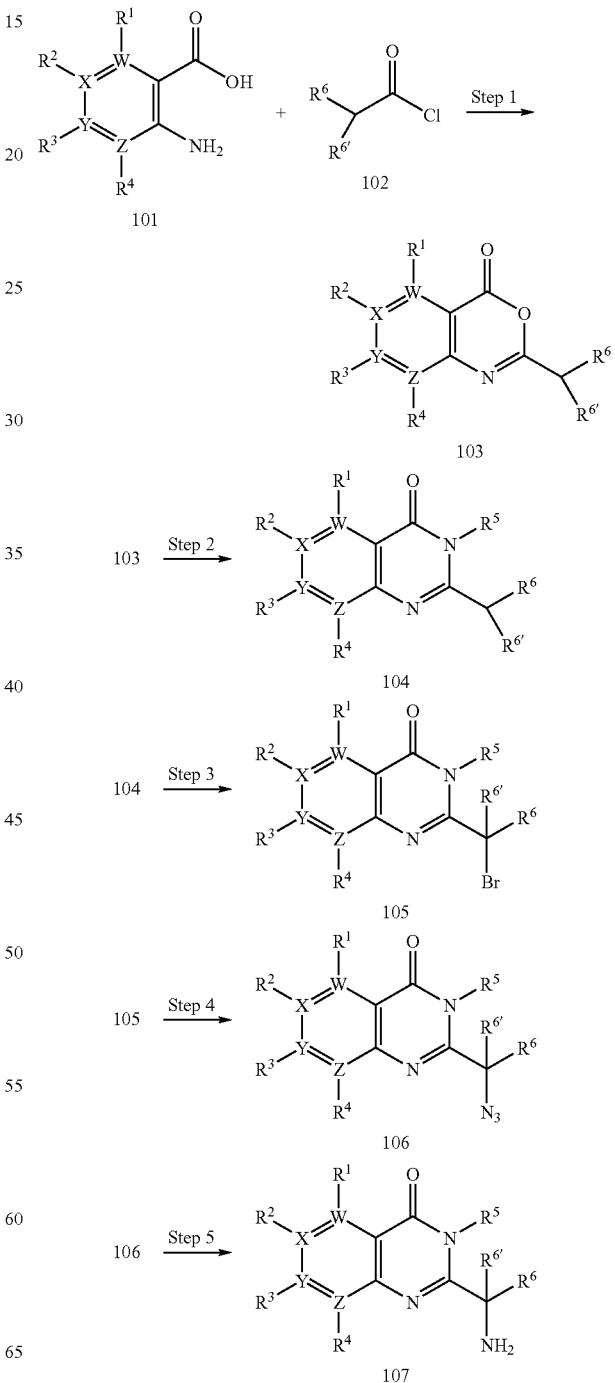

Scheme 3a

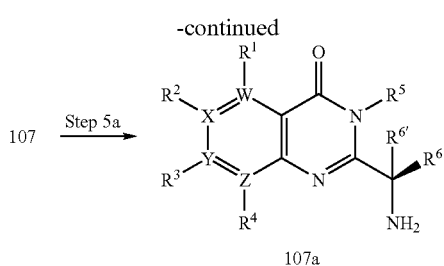

107a

Preparation of Formula 103

Referring to Reaction Scheme 3a, Step 1, to an optionally substituted: amino-nicotinic acid, amino-isonicotinic acid, amino-pyridine-carboxylic acid, amino-pyrazine-carboxylic acid, amino-pyridazine-carboxylic acid and amino-pyrimidine-carboxylic acid (such as 2-amino-nicotinic acid—the compound of Formula 101 where W, X and Y are —C═; Z is —N═; $R^1$, $R^2$ and $R^3$ are H; and $R^4$ is absent) dissolved in an inert organic solvent (such as THF) in the presence of sodium bicarbonate and a dehydrating agent (such as $Na_2SO_4$) is added a slight molar excess of an optionally substituted acid chloride (such as 3-methyl butyryl chloride or isovaleryl chloride—the compound of Formula 102 where $R^6$ is i-propyl and $R^{6'}$ is H), maintaining about room temperature. Completion of the reaction takes place over 2 hours and is monitored, e.g., by TLC. The solvent is then replaced with acetic anhydride, which is heated to about 90–100° C. for about 16 hours, monitoring completion of the reaction (e.g., by TLC) followed by removal of the acetic anhydride under vacuum at about 80–100° C. The reaction mixture is cooled and the corresponding, optionally substituted compound of Formula 103 (such as 2-i-propyl-pyrido[2,3-d][1,3]oxazin-4-one—the compound where W, X and Y are —C═; Z is —N═; $R^1$, $R^2$ and $R^3$ are H; $R^4$ is absent; $R^6$ is i-propyl; and $R^{6'}$ is H) is isolated and purified. Generic nomenclature for the compounds of Formula 103 is as follows:

2-substituted-pyrido[3,2-d][1,3]oxazin-4-one (where W is —N═, and X, Y and Z are —C═),
2-substituted-pyrido[4,3-d][1,3]oxazin-4-one (where X is —N═, and W, Y and Z are —C═),
2-substituted-pyrido[3,4-d][1,3]oxazin-4-one (where Y is —N═, and W, X and Z are —C═),
2-substituted-pyrido[2,3-d][1,3]oxazin-4-one (where Z is —N═, and W, X and Y are —C═),
6-substituted-7-oxa-1,2,5-triaza-naphthalen-8-one (where W and X are —N═, and Y and Z are —C═), and
2-substituted-pyridazino[4,5-d][1,3]oxazin-4-one (where X and Y are —N═, and W and Z are —C═),
7-substituted-pyridazino[3,4-d][1,3]oxazin-5-one (where Y and Z are —N═, and W and X are —C═),
2-substituted-pyazino[2,3-d][1,3]oxazin-4-one (where W and Z are —N═, and X and Y are —C═),
2-substituted-pyrimido[α,β-d][1,3]oxazin-4-one (where W and Y are —N═, and X and Z are —C═) and where (where X and Z are —N═, and W and Y are —C═).

Preparation of Formula 104

Referring to Reaction Scheme 3a, Step 2, about 1.5 molar equivalents of a primary amine of the formula $R^5$—$NH_2$ where $R^5$ is as described above (such as benzylamine) and 1 molar equivalent of a compound of Formula 103 in an inert organic solvent (such as toluene or chloroform) are heated to reflux. The reaction takes place over a period of 1 to 5 hours, preferably 3 hours. After removal of water, ethylene glycol and sodium hydroxide (or sodium carbonate) are added to the reaction mixture and the temperature raised to 110–120° C. Completion of the reaction is monitored, e.g., by TLC. The corresponding, optionally substituted compound of Formula 104 (such as 2-i-propyl-3-benzyl-3H-pyrido[2,3-d]pyrimidin-4-one—where W, X and Y are —C═; Z is —N═; $R^1$, $R^2$ and $R^3$ are H; $R^4$ is absent; $R^5$ is benzyl; $R^6$ is i-propyl; and $R^{6'}$ is H) is isolated and purified. Generic nomenclature for the compounds of Formula 104 is as follows:

3-($R^5$-substituted)-2-($R^6$-substituted)-3H-pyrido[3,2-d]pyrimidin-4-one (where W is —N═, and X, Y and Z are —C═),
3-($R^5$-substituted)-2-($R^6$-substituted)-3H-pyrido[4,3-d]pyrimidin-4-one (where X is —N═, and W, Y and Z are —C═),
3-($R^5$-substituted)-2-($R^6$-substituted)-3H-pyrido[3,4-d]pyrimidin-4-one (where Y is —N═, and W, X and Z are —C═),
3-($R^5$-substituted)-2-($R^6$-substituted)-3H-pyrido[2,3-d]pyrimidin-4-one (where Z is —N═, and W, X and Y are —C═),
7-($R^5$-substituted)-6-($R^6$-substituted)-7H-pyrimido[5,4-c]pyridazin-8-one (where W and X are —N═, and Y and Z are —C═), and
3-($R^5$-substituted)-2-($R^6$-substituted)-3H-pyrimido[5,4-c]pyridazin-8-one (where X and Y are —N═, and W and Z are —C═),
6-($R^5$-substituted)-7-($R^6$-substituted)-6H-pyrimido[4,5-c]pyridazin-5-one (where Y and Z are —N═, and W and X are —C═),
3-($R^5$-substituted)-2-($R^6$-substituted)-3H-pteridin-4-one (where W and Z are —N═, and X and Y are —C═),
3-($R^5$-substituted)-2-($R^6$-substituted)-3H-pyrimido[5,4-d]pyrimidin-4-one (where W and Y are —N═, and X and Z are —C═), and
3-($R^5$-substituted)-2-($R^6$-substituted)-3H-pyrimido[4,5-d]pyrimidin-4-one (where X and Z are —N═, and W and Y are —C═).

Preparation of Formula 105

Referring to Reaction Scheme 3a, Step 3, a compound of Formula 104, dissolved in acetic acid and in the presence of sodium acetate, is heated to 30–50° C., followed by the addition (with agitation) of a slight molar excess of bromine in acetic acid over a period of 2 to 4 hours. Completion is monitored, e.g., by TLC; if the starting material continues to be present, the temperature is increased to 50° C. until completion. The corresponding, optionally substituted compound of Formula 105 (such as 2-(1-bromo-i-propyl)-3-benzyl-3H-pyrido[2,3-d]pyrimidin-4-one—where W, X and Y are —C═; Z is —N═; $R^1$, $R^2$ and $R^3$ are H; $R^4$ is absent; $R^5$ is benzyl; $R^6$ is i-propyl; and $R^{6'}$ is H) is isolated and purified. Other compounds of Formula 105 are (1-bromo-$R^6$-substituted) derivatives otherwise following the generic nomenclature for Formula 104.

Preparation of Formula 106

Referring to Reaction Scheme 3a, Step 4, to 1.5 molar equivalents of sodium azide in an inert organic solvent (such as DMF) is slowly added 1 molar equivalent of a compound of Formula 105. The reaction takes place with agitation at a temperature of 40–60° C. over a period of 3 to 10 hours. Completion is monitored, e.g., by TLC. The corresponding, optionally substituted compound of Formula 106 (such as 2-(1-azido-i-propyl)-3-benzyl-3H-pyrido[2,3-d]pyrimidin-4-one—where W, X and Y are —C═; Z is N $R^1$, $R^2$ and $R^3$ are H; R⁴ is absent; R⁵ is benzyl; R⁶ is i-propyl; and R⁶' is H) is isolated and purified. Other compounds of Formula 106 are (1-azido-R⁶-substituted) derivatives otherwise following the generic nomenclature for Formula 104.

Preparation of Formula 107

Referring to Reaction Scheme 3a, Step 5, to a solution of triphenylphosphine dissolved in an inert organic solvent (such as THF) is added an azide of Formula 106, portionwise over 15 minutes. The reaction takes place with agitation, maintaining the temperature at 20° C. over a period of 5 minutes to 2 hours. The reaction mixture is acidified and solvents removed followed by conventional work up to give the hydrochloride salt of the corresponding, optionally substituted compound of Formula 107 (such as 2-(1-amino-i-propyl)-3-benzyl-3H-pyrido[2,3-d]pyrimidin-4-one—where W, X and Y are —C=; Z is N; R¹, R² and R³ are H; R⁴ is absent; R⁵ is benzyl; R⁶ is i-propyl; and R⁶' is H), which is isolated and purified. Other compounds of Formula 107 are (1-amino-R⁶-substituted) derivatives otherwise following the generic nomenclature for Formula 104.

Preparation of Formula 107a

In certain compounds of the invention, a particular stereoconfiguration can be selected for the R⁶ substituent, such as the (R) isomer, which can be obtained, e.g., as illustrated in optional Step 5a of Reaction Scheme 3a. An amine of Formula 107 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing agitation. The desired isomer, e.g., the (R) isomer illustrated as Formula 107a, is isolated and purified.

Intermediate 1 or analogs thereof such as herein described can be used to prepare compounds of Formula I and II according to Scheme 1a or 1b and as shown in Scheme 3. Thus reductive amination of intermediate 1 by (2-oxo-ethyl)-carbamic acid tert-butyl ester (synthesis described below in Example 1, part (a)) and a reducing agent such as sodium triacetoxyborohydride in a solvent such as dichloromethane gives the corresponding secondary amine which, after isolation and purification, can be further derivatised by acylation for example, with a (substituted) acryoyl chloride in an inert solvent such as dichloromethane in the presence of a tertiary amine base such as triethylamine. The resulting amide derivative is then isolated and purified. Removal of the primary amine protecting group is accomplished under acidic conditions such as with trifluoroacetic acid in dichloromethane and the resulting salt is converted to the amine free base by treatment with, for example, an aqueous solution of a base such as sodium hydrogen carbonate. Heating of the product from the preceding step in an alcoholic solvent such as isopropanol results in the formation of the desired product which is isolated and purified.

EXAMPLES

The following abbreviations and terms have the indicated emeanings throughout: Ac represents acetyl, BNB represents 4-bromomethyl-3-nitrobenzoic acid, Boc represents t-butyloxy carbonyl, Bu represents butyl, c- represents cyclo, CBZ represents carbobenzoxy represents benzyloxycarbonyl, DBU represents diazabicyclo[5.4.0]undec-7-ene, DCM represents dichloromethane methylene chloride represents $CH_2Cl_2$, DCE represents dichloroethylene, DEAD represents diethyl azodicarboxylate, DIC represents diisopronylcarbodiimide, DIEA represents N,N-diisopropylethyl amine, DMAP represents 4-N,N-dimethylaminopyridine, DMF represents N,N-dimethylformamide, DMSO represents dimethyl sulfoxide, DVB represents 1,4-divinylbenzene, EEDQ represents 2-ethoxy-1-ethoxycarbonyl-1,2-dihydroquinoline, Et represents ethyl, Fmoc represents 9-fluorenylmethoxycarbonyl, GC represents gas chromatography, HATU represents O-(7-Azabenzotriazol-1-yl)-1,1,3,3-tetramethyluronium, hexafluorophosphate, HMDS represents hexamethyidisilazane, HOAc represents acetic acid, HOBt represents hydroxybenzotriazole, Me represents methyl, mesyl represents methanesulfonyl, MTBE represents methyl t-butyl ether, NMO represents N-methylmorpholine oxide, PEG represents polyethylene glycol, Ph represents phenyl, PhOH represents phenol, PfP represents pentafluorophenol, PPTS represents pyridinium p-toluenesulfonate, Py represents pyridine, PyBroP represents bromo-tris-pyrrolidino-phosphonium hexafluorophosphate, rt or RT represent room temperature, sat'd represents saturated, s- represents secondary, t- represents tertiary, TBDMS represents t-butyldimethylsilyl, TES represents triethylsilyl, TFA represents trifluoroacetic acid, THF represents tetrahydrofuran, TMOF represents trimethyl orthoformate, TMS represents trimethylsilyl, tosyl represents p-toluenesulfonyl, and Trt represents triphenylmethyl.

Example 1

3-Benzyl-7-chloro-2-[2-methyl-1-(7-oxo-[1,4]diazepan-1-yl)-propyl]-3H-quinazolin-4-one a) Preparation of (2-oxo-ethyl)-carbamic acid tert-butyl ester: To a stirred solution of oxalyl chloride (1.92 mL, 22 mmol) in $CH_2Cl_2$ (40 mL) was added dropwise DMSO (3.12 mL, 44 mmol) at −78° C. After 15 min., a solution of (2-hydroxy-ethyl)-carbamic acid tert-butyl ester (3.22 g, 20 mmol) in $CH_2Cl_2$ (20 mL) was added. After another 45 min., $Et_3N$ (13.9 mL, 100 mmol) was added. The reaction mixture was then warmed to room temperature, diluted with $CH_2Cl_2$ (100 mL), washed with water, 10% HCl, brine, dried and concentrated. Purification by flash chromatography on silica gel (10–15% EtOAc in hexane) gave the title compound (600 mg) as a clear oil: ¹H NMR (400 MHz, CDCl₃) δ9.58 (S, 1H), 5.16 (brs, 1H), 4.02 (s, 2H), 1.46 (s, 9H).

b) Preparation of {2-[1-(3-Benzyl-7-chloro-4-oxo-3,4-dihydro-quinazolin-2-yl)-2-methyl-propylamino]-ethyl}-carbamic acid tert-butyl ester: Sodium triacetoxyborohydride (172 mg, 0.81 mmol) was added to a solution containing 2-(1-amino-2-methyl-propyl)-3-benzyl-7-chloro-3H-quinazolin-4-one (185 mg, 0.54 mmol) (prepared using the general procedure described in WO 0130768) and tert-butyl N-(2-oxoethyl)carbamate (103 mg, 0.65 mmol) in $CH_2Cl_2$ (5.4 mL). The resulting mixture was stirred at room temperature overnight. The reaction was diluted with $CH_2Cl_2$ (10 mL), washed with brine, dried and concentrated under vacuum. Purification by flash chromatography on silica gel (5–10% EtOAc in hexane) gave the title compound (105 mg) as a white solid: MS (ES) m/e 485 (M+H)⁺.

c) (2-{Acryloyl-[1-(3-benzyl-7-chloro-4-oxo-3,4-dihydro-quinazolin-2-yl)-2-methyl-propyl]-amino}-ethyl)-carbamic acid tert-butyl ester: Acryloyl chloride (126 μL, 1.6 mmol) was added to {2-[1-(3-benzyl-7-chloro-4-oxo-3,4-dihydro-quinazolin-2-yl)-2-methyl-propylamino]-ethyl}-carbamic acid tert-butyl ester (500 mg, 1.03 mmol) and $Et_3N$ (216 μL, 0.15 mmol) in $CH_2Cl_2$ (10 mL). The resulting mixture was stirred at room temperature overnight. The reaction mixture was diluted with CH$_2$Cl$_2$ (10 mL), washed with brine, dried and concentrated under vacuum. Purification by flash chromatography on silica gel (10% EtOAc/hexane) gave the title compound (310 mg) as a white solid: MS (ES) m/e 539.2 (M+H)$^+$.

d) N-(2-Amino-ethyl)—N-[1-(3-benzyl-7-chloro-4-oxo-3,4-dihydro-quinazolin-2-yl)-2-methyl-propyl]-acrylamide: (2-{Acryloyl-[1-(3-benzyl-7-chloro-4-oxo-3,4-dihydro-quinazolin-2-yl)-2-methyl-propyl]-amino}-ethyl)-carbamic acid tert-butyl ester (300 mg, 0.56 mmol) was treated with 50% TFA in CH$_2$Cl$_2$ (3 mL at room temperature. After 2 h the mixture was concentrated under vacuum, redissolved in CH$_2$Cl$_2$, washed with 10% NaHCO$_3$, brine, dried and concentrated to give the title compound (240 mg) as a white solid: MS (ES) m/e 439.2 (M+H)$^+$.

e) 3-Benzyl-7-chloro-2-[2-methyl-1-(7-oxo-[1,4]diazepan-1-yl)-propyl]-3H-quinazolin-4-one: A solution of N-(2-Amino-ethyl)—N-[1-(3-benzyl-7-chloro-4-oxo-3,4-dihydro-quinazolin-2-yl)-2-methyl-propyl]-acrylamide (230 mg, 0.53 mmol) in MeOH was refluxed under argon overnight. The reaction mixture was concentrated and the residue purified by flash chromatography on silica gel (2–3% CH$_3$OH in CH$_2$Cl$_2$) to give the title compound (158 mg) as a white foam: MS (ES) m/e 439.0 (M+H)$^+$.

Example 2

3-Benzyl-7-chloro-2-[2-methyl-1-(4-methyl-7-oxo-[1,4]diazepan-1-yl)-propyl]-3H-quinazolin-4-one Iodomethane (23 µL, 0.37 mmol) was added to a solution containing 3-benzyl-7-chloro-2-[2-methyl-1-(7-oxo-[1,4]diazepan-1-yl)-propyl]-3H-quinazolin-4-one and Et$_3$N (51.4 µL, 0.37 mmol) in CH$_2$Cl$_2$ (5 mL). The resulting mixture was stirred at RT overnight, diluted with CH$_2$Cl$_2$ (5 mL), washed with brine, dried and concentrated under vacuum. Purification by flash chromatography on silica gel (1–2% CH$_3$OH in CH$_2$Cl$_2$) gave the title compound (65 mg, 70%) as a pale yellow solid: MS (ES) m/e 453.0 (M+H)$^+$.

Example 3

3-benzyl-7-chloro-2-[(R)-2-methyl-1-(7-oxo-[1,4]diazepan-1-yl)-propyl]-3H-quinazolin-4-one a) (2-{Acryloyl-[(R)-1-(3-benzyl-7-chloro-4-oxo-3,4-dihydro-quinazolin-2-yl)-2-methyl-propyl]-amino}-ethyl)-carbamic acid tert-butyl ester: According to the procedure of Example 1c above, {2-[(R)1-(3-benzyl-7-chloro-4-oxo-3,4-dihydro-quinazolin-2-yl)-2-methyl-propylamino]-ethyl}-carbamic acid tert-butyl ester (211 mg, 0.44 mmol) was converted to the title compound as a white solid: MS (ES) m/e 539.2 (M+H)$^+$.

b) N-(2-Amino-ethyl)-N-[(R)-1-(3-benzyl-7-chloro-4-oxo-3,4-dihydro-quinazolin-2-yl)-2-methyl-propyl]-acrylamide: According to the procedure of Example 1d above, (2-{acryloyl-[(R)-1-(3-benzyl-7-chloro-4-oxo-3,4-dihydro-quinazolin-2-yl)-2-methyl-propyl]-amino}-ethyl)-carbamic acid tert-butyl ester was treated with 50% TFA in CH$_2$Cl$_2$ (3 mL) to give the title compound: MS (ES) m/e 439.2 (M+H)$^+$.

c) 3-Benzyl-7-chloro-2-[(R)-2-methyl-1-(7-oxo-[1,4]diazepan-1-yl)-propyl]-3H-quinazolin-4-one: According to the procedure of Example 1e above, N-(2-amino-ethyl)—N-[(R)-1-(3-benzyl-7-chloro-4-oxo-3,4-dihydro-quinazolin-2-yl)-2-methyl-propyl]-acrylamide was converted to the title compound as a clear oil: MS (ES) m/e 439.0 (M+H)$^+$.

Example 4

2-[1-(Acetyl-7-oxo-[1,4]diazepan-1-yl)-2-methyl-propyl]-3-benzyl-7-chloro-3H-quinazolin-4-one3-Benzyl-7-chloro-2-[2-methyl-1-(7-oxo-[1,4]diazepan-1-yl)-propyl]-3H-quinazolin-4-one from Example 1e above (131 mg, 0.3 mmol) was treated with acetic anhydride (0.8 mL) in pyridine (2 mL) at room temperature overnight. The mixture was diluted with CH$_2$Cl$_2$ (10 mL), washed with H$_2$O, brine, dried and concentrated to give the title compound (120 mg) as an off-white solid: MS (ES) m/e 481.2 (M+H)$^+$.

Example 5

3-Benzyl-7-chloro-2-[1-(3,3-dimethyl-7-oxo-[1,4]diazepan-1-yl)-2-methyl-propyl]-3H-quinazolin-4-one a) ({Acryloyl-[1-(3-benzyl-7-chloro-4-oxo-3,4-dihydro-quinazolin-2-yl)-2-methyl-propyl]-amino}-1,1-demethyl-ethyl)-carbamic acid tert-butyl ester: According to the procedure of Example 1c above, {2-[1-(3-benzyl-7-chloro-4-oxo-3,4-dihydro-quinazolin-2-yl)-2-methyl-propylamino]-1,1-dimethyl-ethyl}-carbamic acid tert-butyl ester (947 mg, 1.85 mmol) was converted to the title compound as a white solid: MS (ES) m/e 567.2 (M+H)$^+$.

b) N-(2-Amino-2-methyl-propyl)—N-[1-(3-benzyl-7-chloro-4-oxo-3,4-dihydro-quinazolin-2-yl)-2-methyl propyl]-acrylamide: According to the procedure of Example 1d above, ({acryloyl-[1-(3-benzyl-7-chloro-4-oxo-3,4-dihydro-quinazolin-2-yl)-2-methyl-propyl]-amino-1,1-dimethyl-ethyl)-carbamic acid tert-butyl ester (730 mg, 1.29 mmol) was treated with 50% TFA in CH$_2$Cl$_2$ (10 mL) to give the title compound: MS (ES) m/e 467.2 (M+H)$^+$.

c) 3-Benzyl-7-chloro-2-[1-(3,3-dimethyl-7-oxo-[1,4]diazepan-1-yl)-2-methyl-propyl]-3H-quinazolin-4-one: According to the procedure of Example 1e above, N-(2-amino-2-methyl-propyl)—N-[1-(3-benzyl-7-chloro-4-oxo-3,4-dihydro-quinazolin-2-yl)-2-methyl propyl]-acrylamide was converted to the title compound as a white solid: MS (ES) m/e 467.0 (M+H)$^+$.

Example 6

3-Benzyl- -2-[1-(4-benzyl-7-oxo-[1,4]diazepan-1-yl)-2-methyl-propyl]-7-chloro-3H-quinazolin-4-one 3-Benzyl-7-chloro-2-[2-methyl-1-(7-oxo-[1,4]diazepan-1-yl)-propyl]-3H-quinazolin-4-one from Example 1e above, (133 mg, 0.30 mmol) was treated with benzyl bromide and Et$_3$N in CH$_2$Cl$_2$ (10 mL) at room temperature overnight. The mixture was diluted with CH$_2$Cl$_2$ (10 mL), washed with H$_2$, brine, dried and concentrated under vacuum. Purification by flash chromatography on silica gel (20% EtOAc/hexane) gave the title compound as a white solid: MS (ES) m/e 529.0 (M+H)$^+$.

Example 7

3-Benzyl-7-chloro-2-[1-(7-oxo-[1,4]diazepan-1 -yl)-propyl]-3H-quinazolin-4-one a) Preparation of {2-[1-(3-benzyl-7-chloro-4-oxo-3,4-dihydro-quinazolin-2-yl)-propylamino]-ethyl}-carbamic acid tert-butyl ester: A mixture of 3-benzyl-2-(1-bromo-propyl)-7-chloro-3H-quinazolin-4-one (3.9 g, 10 mmol) (WO 0130768), (2-amino-ethyl)-carbamic acid tert-butyl ester (2.40 g, 15 mmol) and sodium bicarbonate (1.26 g, 15 mmol) in EtOH (50 mL) was refluxed overnight. The salts were removed by filtration and the filtrate was concentrated to dryness. The residue which remained was purified by flash chromatography on silica gel (10–15% EtOH in hexane) to give the title compound (2.90 g) as a white solid: MS (ES) m/e 471.2 (M+H)$^+$.

b) Preparation of (2-{acryloyl-[1-(3-benzyl-7-chloro-4-oxo-3,4-dihydro-quinazolin-2-yl)-propyl]-amino}-ethyl)-carbamic acid tert-butyl ester: Following the procedure of Example of 1c, 2-[1-(3-benzyl-7-chloro-4-oxo-3,4-dihydro-quinazolin-2-yl)-propylamino]-ethyl}-carbamic acid tert-butyl ester (940 mg, 2 mmol) was converted to the title compound as a white solid: MS (ES) m/e 525.4 (M+H)$^+$.

c) Preparation of N-(2-amino-ethyl)—N-[1-(3-benzyl-7-chloro-4-oxo-3,4-dihydro-quinazolin-2-yl)-propyl]-acrylamide: Following the procedure of Example of 1d, 2-{acryloyl-[1-(3-benzyl-7-chloro-4-oxo-3,4-dihydro-quinazolin-2-yl)-propyl]-amino}-ethyl)-carbamic acid tert-butyl ester was converted to the title compound as a white solid: MS (ES) m/e 425.4 (M+H)$^+$.

d) Preparation of 3-benzyl-7-chloro-2-[1-(7-oxo-[1,4]diazepan-1-yl)-propyl]-3H- quinazolin-4-one: Following the procedure of Example of 1e, N-(2-amino-ethyl)-N-[1-(3-benzyl-7-chloro-4-oxo-3,4-dihydro-quinazolin-2-yl)-propyl]-acrylamide was converted to the title compound as a white solid: MS (ES) m/e 425.2 (M+H)$^+$.

Example 8

3-Benzyl-7-chloro-2-[1-(6,6-dimethyl-7-oxo-[1,4]diazepan-1-yl)-2-methyl-propyl]-3H-quinazolin-4-one a) Preparation of {2-[1-(3-benzyl-7-chloro-4-oxo-3,4-dihydro-quinazolin-2-yl)-2-methyl-propylamino]-ethyl}-carbamic acid tert-butyl ester: Following the procedure of Example 1b, 2-(1-amino-2-methyl-propyl)-3-benzyl-7-chloro-3H-quinazolin-4-one, (2-oxo-ethyl)-carbamic tert-butyl ester and sodium acetoxyborohydride gave the title compound as a white solid: MS (ES) m/e 485.2 (M+H)$^+$.

b) Preparation of {2-[[1-(3-benzyl-7-chloro-4-oxo-3,4-dihydro-quinazolin-2-yl)-2-methyl-propyl]-(3-chloro-2,2-dimethyl-propanoyl)-amino]-ethyl}-carbamic acid tert-butyl ester: {2-[1-(3-Benzyl-7-chloro-4-oxo-3,4-dihydro-quinazolin-2-yl)-2-methyl-propylamino]-ethyl}-carbamic tert-butyl ester (450 mg, 0.93 mmol) was treated with 3-chloropivaloyl chloride (360 μL, 2.80 mmol) and Et$_3$N (388 μl, 2.80 mmol) in CH$_2$Cl$_2$ (10 mL) at room temperature. After 48 h, the mixture was diluted with CH$_2$Cl$_2$ (10 mL), washed with water, brine, dried and concentrated under vacuum. Purification by flash chromatography on silica gel (3–6% EtOAc in hexane) gave the title compound (413 mg) as a clear oil: MS (ES) m/e 603 (M+H)$^+$.

c) Preparation of N-(2-amino-ethyl)-N-[1-(3-benzyl-7-chloro-4-oxo-3,4-dihydro-quinazolin-2-yl)-2-methyl-propyl]-3-chloro-2,2-dimethyl-propionamide: Following the procedure of Example 1d, 2-[[1-(3-benzyl-7-chloro-4-oxo-3,4-dihydro-quinazolin-2-yl)-2-methyl-propyl]-(3-chloro-2,2-dimethyl-propanoyl)-amino]-ethyl}carbamic acid tert-butyl ester was converted to the title compound as a white solid: MS (ES) m/e 503.2 (M+H)$^+$.

d) Preparation of 3-benzyl-7-chloro-2-[1-(6,6-dimethyl-7-oxo-[1,4]diazepan-1-yl)-2-methyl-propyl]-3H-quinazolin-4-one: A mixture of N-(2-amino-ethyl)-N-[1-(3-benzyl-7-chloro-4-oxo-3,4-dihydro-quinazolin-2-yl)-2-methyl-propyl]-3-chloro-2,2-dimethyl-propionamide (300 mg, 0.6 mmol) and potassium hydroxide (40 mg, 0.72 mmol) in EtOH was refluxed overnight. The reaction was concentrated and the residual material was partitioned between CH$_2$Cl$_2$ and water. The organic layer was washed with brine, dried and concentrated under vacuum. Purification by flash chromatography on silica gel (30% EtOAc in hexane) gave the title compound (150 mg) as a white solid: MS (ES) m/e 467.0 (M+H)$^+$.

Example 9

Monopolar Spindle Formation following Application of a KSP Inhibitor

Human tumor cells Skov-3 (ovarian) were plated in 96-well plates at densities of 4,000 cells per well, allowed to adhere for 24 hours, and treated with various concentrations of compounds of the invention for 24 hours. Cells were fixed in 4% formaldehyde and stained with antitubulin antibodies (subsequently recognized using fluorescently-labeled secondary antibody) and Hoechst dye (which stains DNA).

Visual inspection reveealed that the compounds caused cell cycle arrest in the prometaphase stage of mitosis. DNA was condensed and spindle formation had initiated, but arrested cells uniformly displayed monopolar spindles, indicating that there was an inhibition of spindle pole body separation. Microinjection of anti-KSP antibodies also causes mitotic arrest with arrested cells displaying monopolar spindles.

Example 10

Inhibition of Cellular Proliferation in Tumor Cell Lines Treated with KSP Inhibitors Cells were plated in 96-well plates at densities from 1000–2500 cells/well of a 96-well plate and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96® AQ$_{ueous}$ One Solution Cell Proliferation Assay) was used to determine the number of viable cells at $T_0$ and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this. KSP inhibitors inhibited cell proliferation in human ovarian tumor cell lines (SKOV-3).

A Gi$_{50}$ was calculated by plotting the concentration of compound in μM vs the percentage of cell growth of cell growth in treated wells. The Gi$_{50}$ calculated for the compounds is the estimated concentration at which growth is inhibited by 50% compared to control, i.e., the concentration at which:

$$100 \times [(\text{Treated}_{48} - T_0)/(\text{Control}_{48} - T_0)] = 50.$$

All concentrations of compounds are tested in duplicate and controls are averaged over 12 wells. A very similar 96-well plate layout and $Gi_{50}$ calculation scheme is used by the National Cancer Institute (see Monks, et al., J. Natl. Cancer Inst. 83:757–766 (1991)). However, the method by which the National Cancer Institute quantitates cell number does not use MTS, but instead employs alternative methods.

Example 11

Calculation of $IC_{50}$

Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM DTT (Sigma D-9779), 5 µM paclitaxel (Sigma T-7402), 10 ppm antifoam 289 (Sigma A-8436), 25 mM Pipes/KOH pH 6.8 (Sigma P6757), 2 mM MgC12 (VWR JT400301),.and 1 mM EGTA (Sigma E3889). Solution 2 consists of 1 mM NADH (Sigma N8129), 0.2 mg/ml BSA (Sigma A7906), pyruvate kinase 7U/ml, L-lactate dehydrogenase 10 U/ml (Sigma P0294), 100 nM KSP motor domain, 50 µg/ml microtubules, 1 mM DTT (Sigma D9779), 5 µM paclitaxel (Sigma T-7402), 10 ppm antifoam 289 (Sigma A-8436), 25 mM Pipes/KOH pH 6.8 (Sigma P6757), 2 mM MgC12 (VWR JT4003-01), and 1 mM EGTA (Sigma E3889). Serial dilutions (8–12 two-fold dilutions) of the compound are made in a 96-well microtiter plate (Corning Costar 3695) using Solution 1. Following serial dilution each well has 50 µl of Solution 1. The reaction is started by adding 50 µl of solution 2 to each well. This may be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{\text{Range}}{1 + \left(\frac{x}{IC_{50}}\right)^s} + \text{Background}$$

where y is the observed rate and x the compound concentration.

Other compounds of this class were found to inhibit cell proliferation, although $GI_{50}$ values varied. $GI_{50}$ values for the compounds tested ranged from 200 nM to greater than the highest concentration tested. By this we mean that although most of the compounds that inhibited KSP activity biochemically did inhibit cell proliferation, for some, at the highest concentration tested (generally about 20 µM), cell growth was inhibited less than 50%. Many of the compounds have $GI_{50}$ values less than 10 µM, and several have $GI_{50}$ values less than 1 µM. Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation at virtually any concentration may be useful. However, preferably, compounds will have $GI_{50}$ values of less than 1 mM. More preferably, compounds will have $GI_{50}$ values of less than 20 µM. Even more preferably, compounds will have $GI_{50}$ values of less than 10 µM. Further reduction in $GI_{50}$ values may also be desirable, including compounds with $GI_{50}$ values of less than 1 µM. Some of the compounds of the invention inhibit cell proliferation with $GI_{50}$ values from below 200 nM to below 10 nM.

All references and publications, including but not limited to patents and patent applications, cited in this specification are herein incorporated by reference as if each individual reference and publication were specifically and individually indicated to be incorporated by reference herein as though fully set forth.

It is to be understood that the present invention covers all combinations of particular and preferred subgroups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims.

What is claimed:

1. A compound selected from those represented by the formula I:

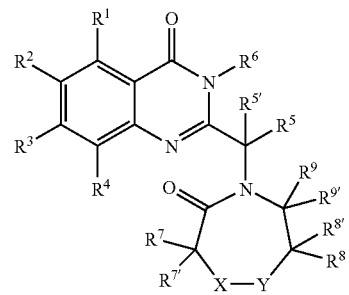

Formula I wherein:
$R^1$, $R^2$, $R^3$ and $R^4$ are each independently chosen from hydrogen, optionally substituted alkyl, optionally substituted alkoxy, halogen, hydroxyl, nitro, cyano, dialkylamino, alkylsulfonyl, alkylsulfonamido, alkylthio, carboxyalkyl, carboxamido, aminocarbonyl, optionally substituted aryl and optionally substituted heteroaryl;

$R^5$ and $R^{5'}$ are each independently chosen from hydrogen, optionally substituted alkyl, optionally substituted aryl, optionally substituted aralkyl, optionally substituted heteroaryl, and optionally substituted heteroaralkyl; or $R^5$ and $R^{5'}$ taken together form an optionally substituted 3- to 7-membered carbocyclic ring;

$R^6$ is hydrogen, optionally substituted alkyl, optionally substituted aryl, optionally substituted aralkyl, optionally substituted heteroaryl, or optionally substituted heteroaralkyl;

$R^7$, $R^{7'}$, $R^8$, $R^{8'}$, $R^9$ and $R^{9'}$ are each independently chosen from hydrogen, optionally substituted alkyl, optionally substituted aryl, optionally substituted aralkyl, optionally substituted heteroaryl, and optionally substituted heteroaralkyl;

one of X and Y is $C(R^{10})(R^{11})$, and the other of X and Y is $N(R^{12})$, wherein $R^{10}$ and $R^{11}$ are each independently chosen from H, optionally substituted alkyl, optionally substituted aryl and optionally substituted heteroaryl; and $R^{12}$ is H, optionally substituted alkyl, optionally substituted aralkyl, optionally substituted heteroaralkyl, optionally substituted alkylcarbonyl, optionally substituted arylcarbonyl, optionally substituted heteroarylcarbonyl, optionally substituted aralkylcarbonyl, optionally substituted heteroaralkylcarbonyl, optionally substituted alkoxycarbonyl, optionally substituted aryloxycarbonyl, optionally substituted heteroaryloxycarbonyl, optionally substituted aralkyloxycarbonyl, or optionally substituted heteroaralkyloxycarbonyl;

wherein the term "heteroaryl" means a 5 or 6 membered heteroaromatic ring containing 1–4 heteroatoms selected from O, N and S; a bicyclic 9 or 10 membered heteroaromatic ring system containing 1–4 heteroatoms selected from O, N and S; or a tricyclic 12–14 membered heteroaromatic ring system containing 1–4 heteroatoms selected from O, N and S;

including single stereoisomers and mixtures of stereoisomers thereof, and pharmaceutically acceptable salts thereof.

2. A compound selected from those represented by the Formula II:

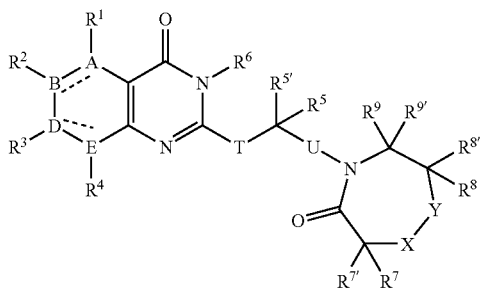

Formula II wherein:

$R^1$, $R^2$, $R^3$ and $R^4$ are each independently chosen from hydrogen, optionally substituted alkyl, optionally substituted alkoxy, halogen, hydroxyl, nitro, cyano, dialkylamino, alkylsulfonyl, alkylsulfonamido, alkylthio, carboxyalkyl, carboxamido, aminocarbonyl, optionally substituted aryl and optionally substituted heteroaryl;

$R^5$ and $R^{5'}$ are each independently chosen from hydrogen, optionally substituted alkyl, optionally substituted aryl, optionally substituted aralkyl, optionally substituted heteroaryl, and optionally substituted heteroaralkyl; or $R^5$ and $R^{5'}$ taken together form an optionally substituted 3- to 7-membered carbocyclic ring;

$R^6$ is hydrogen, optionally substituted alkyl, optionally substituted aryl, optionally substituted aralkyl, optionally substituted heteroaryl, or optionally substituted heteroaralkyl;

$R^7$, $R^{7'}$, $R^8$, $R^{8'}$, $R^9$ and $R^{9'}$ are each independently chosen from hydrogen, optionally substituted alkyl, optionally substituted aryl, optionally substituted aralkyl, optionally substituted heteroaryl, and optionally substituted heteroaralkyl;

one of X and Y is $C(R^{10})(R^{11})$, and the other of X and Y is $N(R^{12})$, wherein $R^{10}$ and $R^{11}$ are each independently chosen from H, optionally substituted alkyl, optionally substituted aryl and optionally substituted heteroaryl; and $R^{12}$ is H, optionally substituted alkyl, optionally substituted aralkyl, optionally substituted heteroaralkyl, optionally substituted alkylcarbonyl, optionally substituted arylcarbonyl, optionally substituted heteroarylcarbonyl, optionally substituted aralkylcarbonyl, optionally substituted heteroaralkylcarbonyl, optionally substituted alkoxycarbonyl, optionally substituted aryloxycarbonyl, optionally substituted heteroaryloxycarbonyl, optionally substituted aralkyloxycarbonyl, or optionally substituted heteroaralkyloxycarbonyl;

T and U are independently a covalent bond, —C(O)—, or optionally substituted alkylene;

A, B, D and E are independently N, C, CH, O, S or absent, provided that:

no more than one of A, B, D or E is absent;

no more than two of A, B, D and E are —N═, and

A, B, D or E can be O or S only when one of A, B, D or E is absent; and provided that $R^1$, $R^2$, $R^3$ or $R^4$ is absent where A, B, D or E, respectively, is —N═, O, S or absent;

including single stereoisomers and mixtures of stereoisomers thereof, and pharmaceutically acceptable salts thereof.

3. A compound or salt according to claim 2 wherein A, B, D and E are independently chosen from —C═ and —N═, T is optionally substituted $C_1$–$C_4$ alkylene or is a covalent bond, and U is optionally substituted $C_1$–$C_4$ alkylene or is a covalent bond.

4. A compound or salt according to claim 3 wherein:

$R^1$, $R^2$, $R^3$ and $R^4$ are each independently selected from H, halogen, cyano, optionally substituted $C_1$–$C_4$ alkyl, $C_1$–$C_4$ haloalkyl, optionally substituted $C_1$–$C_4$ alkoxy, and $C_1$–$C_4$ haloalkoxy;

$R^5$ and $R^{5'}$ are each independently selected from H and $C_1$–$C_4$ alkyl;

$R^6$ is optionally substituted $C_1$–$C_8$ alkyl, optionally substituted aryl-$C_1$–$C_4$ alkyl- or optionally substituted heteroaryl-$C_1$–$C_4$ alkyl;

$R^7$, $R^{7'}$, $R^8$, $R^{8'}$, $R^9$ and $R^{9'}$ are each independently selected from H and $C_1$–$C_4$ alkyl;

$R^{10}$ and $R^{11}$ are each independently selected from H and $C_1$–$C_4$ alkyl; and $R^{12}$ is H, $C_1$–$C_4$ alkyl, optionally substituted aralkyl, optionally substituted heteroaralkyl, $C_1$–$C_6$ alkylcarbonyl, optionally substituted arylcarbonyl, optionally substituted heteroarylcarbonyl, optionally substituted aralkylcarbonyl, optionally substituted heteroaralkylcarbonyl, $C_1$–$C_6$ alkoxycarbonyl, optionally substituted aryloxycarbonyl, optionally substituted heteroaryloxycarbonyl, optionally substituted aralkyloxycarbonyl or optionally substituted heteroaralkyloxycarbonyl, where the optionally substituted aryl or heteroaryl groups or moieties are unsubstituted or substituted with one or more substituents selected from $C_1$–$C_4$ alkyl, $C_1$–$C_4$ haloalkyl, $C_1$–$C_4$ alkoxy, $C_1$–$C_4$ haloalkoxy, amino, $C_1$–$C_4$ alkylamino, di-$C_1$–$C_4$ alkylamino, carboxy, $C_1$–$C_4$ alkylcarbonyloxy, $C_1$–$C_4$ alkoxycarbonyl, carboxamido, $C_1$–$C_4$ alkylcarboxamido, aminocarbonyl, $C_1$–$C_4$ alkylaminocarbonyl, di-$C_1$–$C_4$ alkylaminocarbonyl, cyano, $C_1$–$C_4$ alkylcarbonyl, halogen, hydroxyl, mercapto and nitro.

5. A compound or salt according to claim 2 wherein $R^5$ and $R^{5'}$ are each attached to a stereogenic center having an R-configuration.

6. A compound selected from:
3-Benzyl-7-chloro-2-[2-methyl-1-(7-oxo-[1,4]diazepan-1-yl)-propyl]-3H-quinazolin-4-one;
3-Benzyl-7-chloro-2-[2-methyl-1-(4-methyl-7-oxo-[1,4]diazepan-1-yl)-propyl]-3H-quinazolin-4-one;
3-benzyl-7-chloro-2-[(R)-2-methyl-1-(7-oxo-[1,4]diazepan-1-yl)-propyl]-3H-quinazolin-4-one;
2-[1-(Acetyl-7-oxo-[1,4]diazepan-1-yl)-2-methyl-propyl]-3-benzyl-7-chloro-3H-quinazolin-4-one;
3-Benzyl-7-chloro-2-[1-(3,3-dimethyl-7-oxo-[1,4]diazepan-1-yl)-2-methyl-propyl]-3H-quinazolin-4-one;
3-Benzyl- -2-[1-(4-benzyl-7-oxo-[1,4]diazepan-1-yl)-2-methyl-propyl]-7-chloro-3H-quinazolin-4-one;
3-Benzyl-7-chloro-2-[1-(7-oxo-[1,4]diazepan-1-yl)-propyl]-3H-quinazolin-4-one; and
3-Benzyl-7-chloro-2-[1-(6,6-dimethyl-7-oxo-[1,4]diazepan-1-yl)-2-methyl-propyl]-3H-quinazolin-4-one;
or a pharmaceutically acceptable salt thereof.

7. A composition comprising a pharmaceutically acceptable excipient and a compound or salt according to claim 2.

8. A composition according to claim 7, wherein said composition further comprises an anti-cancer agent selected from taxanes, vinca alkaloids, and topoisomerase I inhibitors.

9. A compound or salt according to claim 4 wherein:
$R^1$, $R^2$, $R^3$ and $R^4$ are each independently selected from H and halogen;
$R^{5'}$ is H and $R^5$ is $C_1$–$C_4$ alkyl;
$R^6$ is optionally substituted phenyl-$C_1$–$C_4$ alkyl-;
$R^9$ and $R^{9'}$ are each H, and $R^7$ and $R^{7'}$ or $R^8$ and $R^{8'}$ are each independently H or $C_1$–$C_4$ alkyl; and
X is $C(R^{10})(R^{11})$, wherein $R^{10}$ and $R^{11}$ are each independently H or $C_1$–$C_4$ alkyl, and Y is $N(R^{12})$, where $R^{12}$ is H, $C_1$–$C_4$ alkyl, aralkyl, heteroaralkyl, $C_1$–$C_6$ alkylcarbonyl, arylcarbonyl, or heteroarylcarbonyl.

10. A compound or salt according to claim 9 wherein:
$R^1$, $R^2$ and $R^4$ are each H and $R^3$ is halogen;
$R^{5'}$ is H and $R^5$ is ethyl, cyclopropyl, iso-propyl or t-butyl;
$R^6$ is optionally substituted benzyl; and
X is $CH_2$, and Y is $N(R^{12})$, where $R^{12}$ is H, methyl, benzyl or acetyl (—C(O)methyl).

11. A compound or salt according to claim 1 wherein:
$R^1$, $R^2$, $R^3$ and $R^4$ are each independently selected from H, halogen, cyano, optionally substituted $C_1$–$C_4$ alkyl, $C_1$–$C_4$ haloalkyl, optionally substituted $C_1$–$C_4$ alkoxy, and $C_1$–$C_4$ haloalkoxy;
$R^5$ and $R^{5'}$ are each independently selected from H and $C_1$–$C_4$ alkyl;
$R^6$ is optionally substituted $C_1$–$C_8$ alkyl, optionally substituted aryl-$C_1$–$C_4$ alkyl- or optionally substituted heteroaryl-$C_1$–$C_4$ alkyl;
$R^7$, $R^{7'}$, $R^8$, $R^{8'}$, $R^9$ and $R^{9'}$ are each independently selected from H and $C_1$–$C_4$ alkyl;
$R^{10}$ and $R^{11}$ are each independently selected from H and $C_1$–$C_4$ alkyl; and
$R^{12}$ is H, $C_1$–$C_4$ alkyl, optionally substituted aralkyl, optionally substituted heteroaralkyl, $C_1$–$C_6$ alkylcarbonyl, optionally substituted arylcarbonyl, optionally substituted heteroarylcarbonyl, optionally substituted aralkylcarbonyl, optionally substituted heteroaralkylcarbonyl, $C_1$–$C_6$ alkoxycarbonyl, optionally substituted aryloxycarbonyl, optionally substituted heteroaryloxycarbonyl, optionally substituted aralkyloxycarbonyl or optionally substituted heteroaralkyloxycarbonyl, where the optionally substituted aryl or heteroaryl groups or moieties are unsubstituted or substituted with one or more substituents selected from $C_1$–$C_4$ alkyl, $C_1$–$C_4$ haloalkyl, $C_1$–$C_4$ alkoxy, $C_1$–$C_4$ haloalkoxy, amino, $C_1$–$C_4$ alkylamino, di-$C_1$–$C_4$ alkylamino, carboxy, $C_1$–$C_4$ alkylcarbonyloxy, $C_1$–$C_4$ alkoxycarbonyl, carboxamido, $C_1$–$C_4$ alkylcarboxamido, aminocarbonyl, $C_1$–$C_4$ alkylaminocarbonyl, di-$C_1$–$C_4$ alkylaminocarbonyl, cyano, $C_1$–$C_4$ alkylcarbonyl, halogen, hydroxyl, mercapto and nitro.

12. A compound according to claim 11 wherein:
$R^1$, $R^2$, $R^3$ and $R^4$ are each independently selected from H and halogen;
$R^{5'}$ is H and $R^5$ is $C_1$–$C_4$ alkyl;
$R^6$ is optionally substituted phenyl-$C_1$–$C_4$ alkyl-;
$R^9$ and $R^{9'}$ are each H, and $R^7$ and $R^{7'}$ or $R^8$ and $R^{8'}$ are each independently H or $C_1$–$C_4$ alkyl; and
X is $C(R^{10})(R^{11})$, wherein $R^{10}$ and $R^{11}$ are each independently H or $C_1$–$C_4$ alkyl, and Y is $N(R^{12})$, where $R^{12}$ is H, $C_1$–$C_4$ alkyl, aralkyl, heteroaralkyl, $C_1$–$C_6$ alkylcarbonyl, arylcarbonyl, or heteroarylcarbonyl.

13. A compound according to claim 12 wherein:
$R^1$, $R^2$, and $R^4$ are each H and $R^3$ is halogen;
$R^{5'}$ is H and $R^5$ is ethyl, cyclopropyl, iso-propyl or t-butyl;
$R^6$ is optionally substituted benzyl; and
X is $CH_2$, and Y is $N(R^{12})$, where $R^{12}$ is H, methyl, benzyl or acetyl (—C(O)methyl).

* * * * *